United States Patent
Ruddy et al.

(10) Patent No.: US 11,898,114 B2
(45) Date of Patent: Feb. 13, 2024

(54) REACTIONS AND METHODS FOR PRODUCING FUELS

(71) Applicant: Alliance for Sustainable Energy, LLC, Golden, CO (US)

(72) Inventors: Daniel Ruddy, Arvada, CO (US); Thomas Dwight Foust, Evergreen, CO (US); Trenton John Wilke, Seattle, WA (US); Anh The To, Denver, CO (US); Andrew Wolf Bartling, Golden, CO (US); Martha Arellano-Trevino, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/546,170

(22) Filed: Dec. 9, 2021

(65) Prior Publication Data
US 2022/0195322 A1 Jun. 23, 2022

Related U.S. Application Data

(60) Provisional application No. 63/124,173, filed on Dec. 11, 2020.

(51) Int. Cl.
*C10L 1/185* (2006.01)
*C10L 10/12* (2006.01)
(Continued)

(52) U.S. Cl.
CPC ............ *C10L 1/1852* (2013.01); *C07C 41/14* (2013.01); *C10L 10/12* (2013.01); *C10L 10/06* (2013.01); *C10L 2200/0446* (2013.01)

(58) Field of Classification Search
CPC ........ C07C 41/14; C10L 1/1852; C10L 10/12; C10L 10/06; C10L 2200/0446
See application file for complete search history.

(56) References Cited

U.S. PATENT DOCUMENTS 2,449,469 A * 9/1948 Gresham ................. C07C 41/56
568/601
5,746,785 A * 5/1998 Moulton ................. C10L 10/08
44/443

(Continued)

FOREIGN PATENT DOCUMENTS

| CN | 105753666 A | 7/2016 | |
|---|---|---|---|
| EP | 2 905 293 A1 | 8/2015 | |
| WO | WO-2020120834 A1 * | 6/2020 | ............... C10G 3/47 |

OTHER PUBLICATIONS

Majewski et al. "What is Diesel Fuel". DieselNet Technology Guide. May 2020.https://dieselnet.com/tech/fuel_diesel.php#:~:text=Diesel%20fuel%20is%20a%20mixture%20of%20hydrocarbons%E2%80%94with%20boiling%20points,which%20are%20obtained%20from%20petroleum. (Year: 2020).*

(Continued)

*Primary Examiner* — Latosha Hines
(74) *Attorney, Agent, or Firm* — Michael A. McIntyre

(57) ABSTRACT

The present disclosure relates to a composition that includes a compound having the structure $R_1O-(CH_2O)_n-R_2$ and a cetane number between about 65 and about 100, where n is between 1 and 10, inclusively, $R_1$ includes a first alkyl group, and $R_2$ includes a second alkyl group.

14 Claims, 21 Drawing Sheets

(51) Int. Cl.
   *C07C 41/14* (2006.01)
   *C10L 10/06* (2006.01)

(56) References Cited

U.S. PATENT DOCUMENTS

| | | | |
|---|---|---|---|
| 9,090,842 | B2 | 7/2015 | Hong et al. |
| 2014/0364653 | A1 | 12/2014 | Shang et al. |
| 2022/0049174 | A1* | 2/2022 | Kouva .................... C10L 1/026 |

OTHER PUBLICATIONS

Badia et al., "Catalytic Activity and Accessibility of Acidic Ion-Exchange Resins in Liquid Phase Etherification Reactions", Topics in Catalysis, 2015, vol. 58, No. 14, pp. 919-932.
Baranowski et al., "Synthesis of Polyoxymethylene Dimethyl Ethers (OME): A Review", Applied Catalysis B: Environmental, 2017, vol. 217, pp. 407-420.
Burger et al., "Poly(Oxymethylene) Dimethyl Ethers as Components of Tailored Diesel Fuel: Properties, Synthesis and Purification Concepts", Fuel 2010, vol. 89, No. 11, pp. 3315-3319.
Burger et al., "Chemical Equilibrium and Reaction Kinetics of the Heterogeneously Catalyzed Formation of Poly (oxymethylene) Dimethyl Ethers from Methylal and Trioxane", Industrial & Engineering Chemistry Research, 2012, vol. 51, pp. 12751-12761.
Christensen et al., "Renewable Oxygenate Blending Effects on Gasoline Properties", Energy & Fuels, 2011, vol. 25, No. 10, pp. 4723-4733.
Ezeji et al., "Bioproduction of Butanol from Biomass: FromGenes to Bioreactors", Current Opinion in Biotechnology, Jun. 2007, vol. 18, No. 3, pp. 220-227.
Fioroni et al., "Screening of Potential Biomass-Derived Streams as Fuel Blendstocks for Mixing Controlled Compression Ignition Combustion", SAE International Journal of Advances and Current Practices in Mobility, Apr. 2019, vol. 1, No. 3, pp. 1117-1138.
Grim et al., "Growing the Bioeconomy through Catalysis: A Review of Recent Advancements in the Production of Fuels and Chemicals from Syngas-Derived Oxygenates", ACS Catalysis, 2019, vol. 9, No. 5, pp. 4145-4172.
Hafenstine et al., "Single-Phase Catalysis for Reductive Etherification of Diesel Bioblendstocks", Green Chemistry, Jul. 2020, vol. 22, No. 14, pp. 4463-4472.
Haltenort et al., "(Trans)acetalization Reactions for the Synthesis of Oligomeric Oxymethylene Dialkyl Ethers Catalyzed by Zeolite BEA25", Topics in Catalysis, Jun. 2019, vol. 62, pp. 551-559.
Härtl et al., "Oxygenate screening on a heavy-duty diesel engine and emission characteristics of highly oxygenated oxymethylene ether fuel OME1", Fuel, 2015, vol. 153, pp. 328-335.
Härtl et al., "Oxymethylene Ether as Potentially CO2-Neutral Fuel for Clean Diesel Engines Part 1: Engine Testing", MTZ Worldwide, 2017, vol. 78, No. 2, pp. 52-59.
Huo et al., Tailoring Diesel Bioblendstock from Integrated Catalytic Upgrading of Carboxylic Acids: A "Fuel Property First" Approach. Green Chemistry, Nov. 2019, vol. 21, No. 21, pp. 5813-5827.
Kang et al., "Synthesis and Physicochemical Characterization of Polyoxymethylene Dimethyl Ethers", Journal of Fuel Chemistry and Technology, 2017, vol. 45, No. 7, pp. 837-845.
Kass et al., "Compatibility of Elastomers with Polyoxymethylene Dimethyl Ethers and Blends with Diesel", SAE Technical Paper Series, SAE International Journal of Advances and Current Practices in Mobility, 2020, vol. 2, No. 4, pp. 1963-1973.
Khan et al. "Bioenergy Production From Plant Biomass: Bioethanol From Concept To Reality", Nature Procedings, 2011, pp. 1-13.
Kummara et al., "Isotope Effect on the Melt-Isothermal Crystallization of Polyoxymethylene D/H Random Copolymers and D/H Blend Samples", Macromolecules, 2015, vol. 48, pp. 8070-8081.
Lautenschütz et al., "Physico-chemical properties and fuel characteristics of oxymethylenedialkyl ethers", Fuel, 2016, vol. 173, pp. 129-137.
Liu et al., "Performance, Combustion and Emission Characteristics of Polyoxymethylene Dimethyl Ethers (PODE3-4)/Wide Distillation Fuel (WDF) Blends in Premixed Low Temperature Combustion (LTC)", SAE International Journal of Fuels and Lubricants, Jun. 2015, vol. 8, No. 2, pp. 298-306.
McEnally et al., "Sooting tendencies of co-optima test gasolines and their surrogates", Proceedings of the Combustion Institute, 2019, vol. 37, No. 1, pp. 961-968.
Omari et al., "Potential of Long-Chain Oxymethylene Ether and Oxymethylene Ether-Diesel Blends for Ultra-Low Emission Engines", Applied Energy, Apr. 2019, vol. 239, pp. 1242-1249.
Pérez et al., "Ion Exchange Resins as Catalysts for the Liquid-Phase Dehydration of 1-Butanol to Di-n-Butyl Ether", Applied Catalysis A; General, Jul. 2014, vol. 482, pp. 38-48.
Ramírez et al., "Role of Ion-Exchange Resins as Catalyst in the Reaction-Network of Transformation of Biomass into Biofuels", Journal of Chemical Technology and Biotechnology, Jun. 2017, vol. 92, No. 11, pp. 2775-2786.
To et al., "Dehydrogenative Coupling of Methanol for the Gas-Phase, One-Step Synthesis of Dimethoxymethane over Supported Copper Catalysts", ACS Sustainable Chemistry & Engineering, 2020, vol. 8, No. 32, pp. 12151-12160.
Wang et al., "Mg—Al Mixed Oxide Derived from Hydrotalcites Prepared Using the Solvent-Free Method: A Stable Acid-Base Bifunctional Catalyst for Continuous-Flow Transesterification of Dimethyl Carbonate and Ethanol", Industrial & Engineering Chemistry Research, 2020, vol. 59, pp. 5591-5600.
Wu et al., "Production of Fuels and Chemicals from Biomass: Condensation Reactions and Beyond", Chem, 2016, vol. 1, No. 1, pp. 32-58.
Yang et al., "Phenylsulfonic Acid Functionalized Mesoporous Silica Catalyzed Transetherification of Alcohols with Dimethoxymethane", Chinese Journal of Chemistry, 2005, vol. 23, pp. 349-352.
Huq et al., "Performance-advantaged ether diesel bioblendstock production by a priori design", PNAS, 2019, vol. 116, No. 52, pp. 26421-26430.

* cited by examiner

REACTIONS AND METHODS FOR PRODUCING FUELS

CROSS-REFERENCE TO RELATED APPLICATIONS

This application claims priority from U.S. Provisional Patent Application No. 63/124,173 filed on Dec. 11, 2020, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Heavy-duty truck vehicle miles traveled in the U.S., which rely on diesel-fueled compression ignition (CI) engines, are expected to increase 38% by 2050. However, vehicle efficiency standards are being implemented to maintain energy/fuel at current levels, which will drive a significant improvement in energy intensity (i.e., energy per ton-mile traveled). Enhanced fuel properties play a major role in the improvement of fuel economy and engine efficiency. Simultaneously, low-net-carbon and low-emission (e.g., soot, $NO_x$) fuels are required to meet the fuel demand in an environmentally conscious and sustainable way. Thus, there remains a need for improved liquid fuels and methods for producing them.

SUMMARY

An aspect of the present disclosure is a composition that includes a compound having the structure $R_1O$—$(CH_2O)_n$—$R_2$ and a cetane number between about 65 and about 100, where n is between 1 and 10, inclusively, $R_1$ includes a first alkyl group, and $R_2$ includes a second alkyl group. In some embodiments of the present disclosure, the composition may further include a lower heating value between about 30 MJ/kg and about 45 MJ/kg. In some embodiments of the present disclosure, the composition may further include a flash point temperature between about 55° C. and about −25° C. In some embodiments of the present disclosure, the composition may further include a cloud point temperature between about −65° C. and about 70° C. In some embodiments of the present disclosure, the composition may further include a yield sooting index (YSI) between about 20 and about 50. In some embodiments of the present disclosure, the composition may further include a water solubility between about 0.1 g/L and 20 g/L.

In some embodiments of the present disclosure, $R_1$ may include between 1 and 10 carbon atoms. In some embodiments of the present disclosure, $R_2$ may include between 1 and 10 carbon atoms. In some embodiments of the present disclosure, $R_1$ may include a first butyl group. In some embodiments of the present disclosure, the first butyl group may include at least one of 1-butyl, iso-butyl, and/or sec-butyl. In some embodiments of the present disclosure, $R_1$ may include a first pentyl group. In some embodiments of the present disclosure, the first pentyl group may include at least one of n-pentyl, iso-pentyl, and/or neo-pentyl. In some embodiments of the present disclosure, $R_2$ may include a second butyl group. In some embodiments of the present disclosure, the second butyl group may include at least one of 1-butyl, iso-butyl, and/or sec-butyl. In some embodiments of the present disclosure, $R_2$ may include a second pentyl group. In some embodiments of the present disclosure, the second pentyl group may include at least one of n-pentyl, iso-pentyl, and/or neo-pentyl. In some embodiments of the present disclosure, n may be between 1 and 6, inclusively.

An aspect of the present disclosure is a composition that includes at least one of $BuO(CH_2O)Bu$, $MeO(CH_2O)_2Bu$, and/or $BuO(CH_2O)_2Bu$, where Bu represents at least one of an n-butyl group, an iso-butyl group, and/or a sec-butyl group and Me represents a methyl group, and a cetane number between about 45 and about 100.

An aspect of the present disclosure is a composition that includes at least one of $PeO(CH_2O)Pe$, $MeO(CH_2O)_2Pe$, $PeO(CH_2O)_2Pe$, or $MeO(CH_2O)_3Pe$, where Pe represents at least one of an n-pentyl group, an iso-pentyl group, and/or a neo-pentyl group and Me represents a methyl group, and a cetane number between about 50 and about 100.

An aspect of the present disclosure is a method that includes completing a reaction that includes an ether and an alcohol to form a compound having the structure $R_1O$—$(CH_2O)_n$—$R_2$, where n is between 1 and 10, inclusively, $R_1$ includes a first alkyl group, and $R_2$ includes a second alkyl group.

BRIEF DESCRIPTION OF DRAWINGS

Some embodiments are illustrated in referenced figures of the drawings. It is intended that the embodiments and figures disclosed herein are to be considered illustrative rather than limiting.

DETAILED DESCRIPTION

Figure 1:
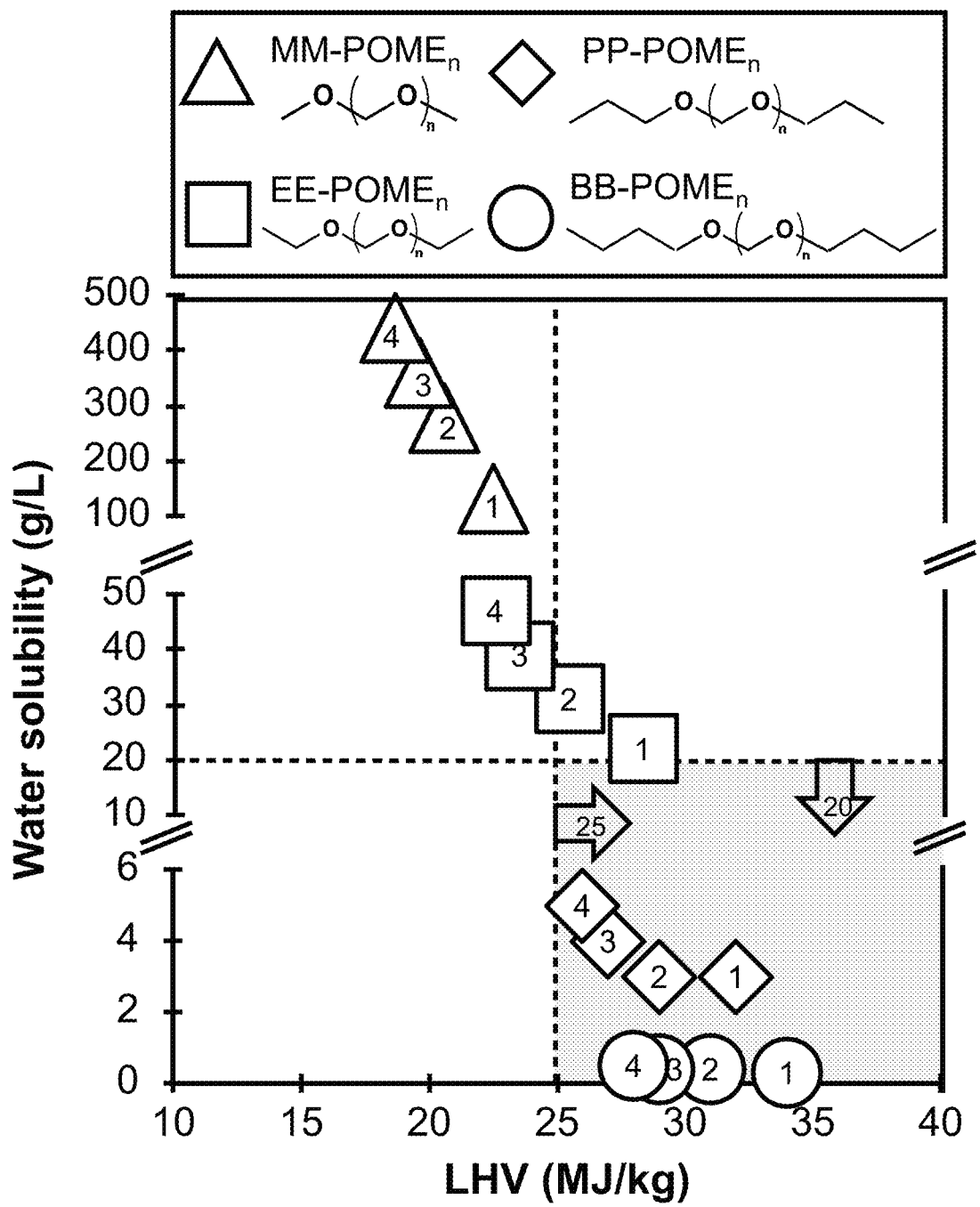
FIG. 1 illustrates predicted and measured water solubilities (g/L) and lower heating values (LHVs) (MJ/kg) of ethyl (EE), propyl (PP) and butyl (BB) exchanged MM-$POME_n$ (n=1-4), according to some embodiments of the present disclosure (POME=poly(oxymethylene) ether). Diesel blend stock fuel property criteria limits are represented by dotted lines. Chain lengths (n=1-4) within the same end-group are represented by the increased numeration within the same marker type. Detailed values are summarized in Table 14.

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

Among other things, the present disclosure relates to methods and catalysts for reacting and/or exchanging the alkoxy end-groups in poly(oxymethylene) ethers (POMEs) to produce products having favorable physical properties and/or performance metrics as liquid fuels and/or liquid fuel additives. As described herein, in some embodiments of the present disclosure, such reactions may be catalyzed using a solid acid catalyst under mild reaction conditions such as low temperatures (e.g., between about 20° C. and about 100° C.) and low pressures (e.g., between about 1 atm and about 2 atm (gauge)). The process enables fuel property tuning of the POMEs molecules, providing, among other things, diesel fuel blend stock mixtures having at least one of low soot producing tendencies, decreased water solubilities, and/or increased heating values.

For example, in some embodiments of the present disclosure, a composition suitable for use as a fuel and/or fuel blend stock, among other liquid products and intermediates, may include a compound having the structure R$_1$O—(CH$_2$O)$_n$—R$_2$ where n is between 1 and 10, inclusively, R$_1$ includes a first alkyl group, R$_2$ includes a second alkyl group, and having at least one superior physical property and/or performance metric. Examples of superior physical properties and/or performance metrics include cetane number, lower heating value (LHV), flash point, cloud point, yield sooting index (YSI), and water solubility. In some embodiments of the present disclosure, a composition (e.g., fuel and/or fuel blend stock) that includes a compound having the structure $R_1O—(CH_2O)_n—R_2$ may have a cetane value between about 65 and about 100. In some embodiments of the present disclosure, a composition may have a lower heating value between about 30 MJ/kg and about 45 MJ/kg. In some embodiments of the present disclosure, a composition may have a flash point temperature between about 55° C. and about −25° C. In some embodiments of the present disclosure, a composition may have a cloud point temperature between about −65° C. and about 70° C. In some embodiments of the present disclosure, a composition may have a yield sooting index (YSI) between about 20 and about 50. In some embodiments of the present disclosure, a composition that includes a compound having the structure $R_1O—(CH_2O)_n—R_2$ may have a water solubility between about 0.1 g/L and 20 g/L.

The structure $R_1O—(CH_2O)_n—R_2$, where n is between 1 and 10, inclusively, with $R_1$ a first alkyl group and $R_2$ a second alkyl group, defines an ether, more specifically an alkyl terminated polyoxymethylene ether. In some embodiments of the present disclosure, the number of oxymethylene repeat units, $—(CH_2O)_n—$, may be between about 1 and 6 ($1 \le n \le 6$). In some embodiments of the present disclosure, the alkyl groups terminating a polyoxymethylene ether may be the same alkyl group or different alkyl groups. For example, at least one of $R_1$ and/or $R_2$ may include a hydrocarbon having between 1 and 10 carbon atoms, inclusively. In some embodiments, the hydrocarbon may be a straight-chained hydrocarbon and/or a branched hydrocarbon. Examples of straight-chained hydrocarbons include methyl, ethyl, n-propyl, n-butyl, n-pentyl, n-hexyl groups, etc. up to a total of about 10 carbon atoms. Examples of branched-chained hydrocarbons include iso-butyl, sec-butyl, iso-propyl, 1-methylpropyl, 2-methylpropyl, 1-methylbutyl, 2-methylbutyl, 3-methylbutyl, iso-pentyl, neo-pentyl, etc., up to a total of about 10 carbon atoms.

As shown herein, in some embodiments of the present disclosure, $R_1$ may be a butyl group (e.g., 1-butyl (i.e., n-butyl), iso-butyl, and/or sec-butyl) may be at a concentration between 0 mol % and 100 mol %, inclusively, with the remainder being an alkyl group other than a butyl group and/or a different butyl group. Unless specified otherwise the term "butyl" or the abbreviations "Bu" and "B" refer to the 1-butyl (i.e., n-butyl) group. Similarly, in some embodiments of the present disclosure, $R_2$ may be a butyl group at a concentration between 0 mol % and 100 mol %, inclusively, with the remainder being an alkyl group other than a butyl group. $R_2$ may be the same group as $R_1$, or $R_2$ may be different than $R_1$. As shown above, an alkyl terminated polyoxymethylene ether may be shown as $R_1O—(CH_2O)_n—R_2$. Another equivalent representation is as $RO—(CH_2O)_{n-1}—CH_2—OR$, where R is an alkyl group as defined above for $R_1$ and $R_2$. Using this second representation, in some embodiments of the present disclosure, R may include one or more alkyl groups. For example, in some embodiments of the present disclosure, R may include a butyl group (e.g., 1-butyl, iso-butyl, and/or sec-butyl) at a concentration between 0 mol % and 100 mol %, inclusively, with the remainder being an alkyl group other than a butyl group. In some embodiments of the present disclosure, R may include a butyl group at a concentration between 0 mol % and 100 mol %, inclusively, with the remainder being a methyl group. In some embodiments of the present disclosure, at least one of $R_1$ or $R_2$ may be a pentyl group isomer: e.g., at least one of n-pentyl, iso-pentyl, or neo-pentyl.

As described above, a variety of alkyl terminated polyoxymethylene molecules may be produced for use as fuels and/or fuel blend stocks. In some embodiments of the present disclosure, such molecules may be synthesized by Reaction 1 below, by reacting at least one starting alkyl terminated polyoxymethylene molecule with at least one alcohol:

Reaction 1

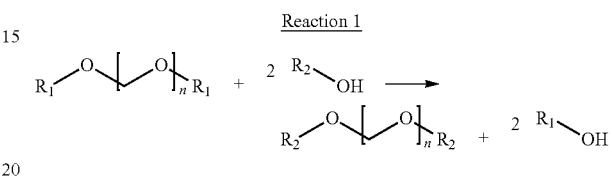

Here, n may be between 1 and 10, inclusively, $R_1$ may include a first alkyl group, and $R_2$ may include a second alkyl group, as described above. For example, $R_1$ may include a methyl group and $R_2$ may include a butyl group. In some embodiments of the present disclosure, the exchange of $R_1$ for $R_2$ may be complete (i.e., 100 mol %) or some percentage less than 100 mol %. Incomplete reactions may be represented by Reactions 2 and 3 (note that these two reactions result in equivalent final products).

Reaction 2

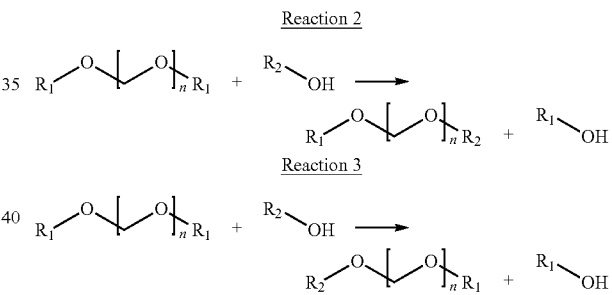

Reaction 3

As shown herein, the percent completion of Reaction 1 may be determined by controlling the ratio of the reactants, i.e., the alcohol and the starting alkyl terminated polyoxymethylene molecule. In some embodiments of the present disclosure, the ratio of alcohol to the starting alkyl terminated polyoxymethylene molecule may be varied between about 50:1 and about 1:1, or between about 10:1 and about 2:1.

Accordingly, as described in more detail below, an acid-catalyzed trans-acetalization reaction was developed to exchange the methyl end-groups of dimethyl terminated polyoxymethylene ethers, $CH_3O—(CH_2O)_n—CH_3$, abbreviated as MM-POMEs (n=3-6) or MM-POME$_{3-6}$, with butyl end-groups, $CH_3(CH_2)_3O—(CH_2O)_n—(CH_2)_3CH_3$, abbreviated as BB-POMEs (n=1-6) or BB-POME$_{1-6}$. Although n-butyl end-groups are shown here, iso-butyl, sec-butyl, iso-pentyl, and/or neo-pentyl end groups, or any other alkyl end group of choice, may also be used, as shown in more detail below. In some embodiments of the present disclosure, the reaction utilized an ion-exchange resin (e.g., a sulfonic acid functionalized styrenic divinyl benzene resin from the Amberlyst series) as the acid catalyst at mild reaction conditions of about 60° C. and about atmospheric pressure. Approximately 100 mL of butyl-exchanged POMEs in the diesel boiling range were produced, enabling laboratory-scale fuel property testing. Among other things, the butyl-terminated POME mixture possesses the advantaged fuel properties of the parent MINI-POMEs (low-soot, high-cetane) while exhibiting improved energy density (Lower Heating Value (LHV)=30 MJ/kg) and substantially reduced water solubility (7.3 g/L) compared to the parent MM-POME mixture (LHV=19 MJ/kg, water solubility of 258 g/L).

As shown herein, pure POME compounds and/or mixtures of two or more POME compounds can provide fuels and/or fuel blend stocks having superior physical properties and/or performance metrics when compared to other materials. A set of blend stock screening criteria, termed Tier 1, has been defined based on previously reported fuel characteristics for compression ignition (CI) fuels (see Table 1 below). The ASTM specification for diesel fuel oils (ASTM D975-20a) stipulates a diesel boiling range between 180° C. and 338° C.; however, Tier 1 extends the boiling range to between 160° C. and 338° C. where the lower value is dictated by the upper limit requirements of the fuel blend stocks for advanced spark-ignition (gasoline) engines and the higher value represents the diesel T90 upper limit dictated by the ASTM specification. The limit for cloud point ($T_{cloud}$) is less than 0° C., to ensure operability at low temperatures in engines and along the fueling infrastructure. The Tier 1 criteria specify that an important safety property is a flash point greater than 52° C. to ensure safe handling at normal atmospheric conditions as stipulated by ASTM D975-20a. CN values of at least 40 are required to ensure ignition quality and meet the ASTM D975-20a specification. YSI values, a measure of the tendency of a fuel to form soot when combusted, are targeted to be below the value for a certification diesel fuel of 246. A greater LHV results in improved fuel economy, and the Tier 1 criterion stipulates at least 25 MJ/kg, which is comparable to the LHV reported for ethanol (26.8 MJ/kg). This criterion ensures that the LHV penalty of a new diesel blend stock will be comparable to that of E10 gasoline. Finally, the water solubility criterion is less than 20 g/L to prevent phase separation in the distribution system and minimize potential groundwater contamination.

TABLE 1

Tier 1 criteria for compression ignition (CI) fuel properties.

| Fuel Property | Criteria Limit |
| --- | --- |
| Boiling point (° C.) | 160-338 |
| Cloud Point (° C.) | <0 |
| Flash point (° C.) | >52 |
| Cetane number | ≥40 |
| YSI | <246 |
| LHV (MJ/kg) | <25 |
| Water solubility (g/L) | <20 |

The development of bio-derived CI fuels can benefit from a fuel-property-first approach. In addition to the POME chain length noted above, the alkyl-terminating group also affects the fuel properties. This approach is at least partially based on the hypothesis that end-group exchange of MM-POMEs with larger alcohols, such as 1-propanol and 1-butanol (BuOH), could further benefit the resultant fuel properties, especially by decreasing the water solubility due to the incorporation of larger hydrophobic moieties. Importantly, these alcohols can also be renewably sourced, especially ethanol and butanol (e.g., 1-butanol, iso-butanol, and/or sec-butanol). The notation used herein of MM-, EE-, PP-, and BB-POME$_n$ refer to two methyl, two ethyl, two propyl and two butyl end-groups (butyl refers to the linear n-butyl terminated POME unless noted otherwise), respectively, with n referring to the number of oxymethylene repeat units. The results were compared to the Tier 1 criteria enabling trends to be identified across chain length (n=1-4) and end-group. The properties of LHV and water solubility were problematic for the parent MM-POME$_n$ structures, and a clearly visible advantage can be observed in the calculated improvements when incorporating longer alkyl end-groups (see FIG. 1). Specifically, BB-POME$_{1-4}$ (pure component POMEs and/or mixtures of POMEs having between 1 and 4 repeat units, —(CH$_2$O)$_n$—, terminated on both ends by butyl end groups) possessed the most desirable properties, especially considering the critical water solubility metric, motivating the development of chemistry to upgrade a MM-POME$_n$ mixture into a product having enhanced fuel properties.

Catalytic End-Group Exchange.

Figure 2A:
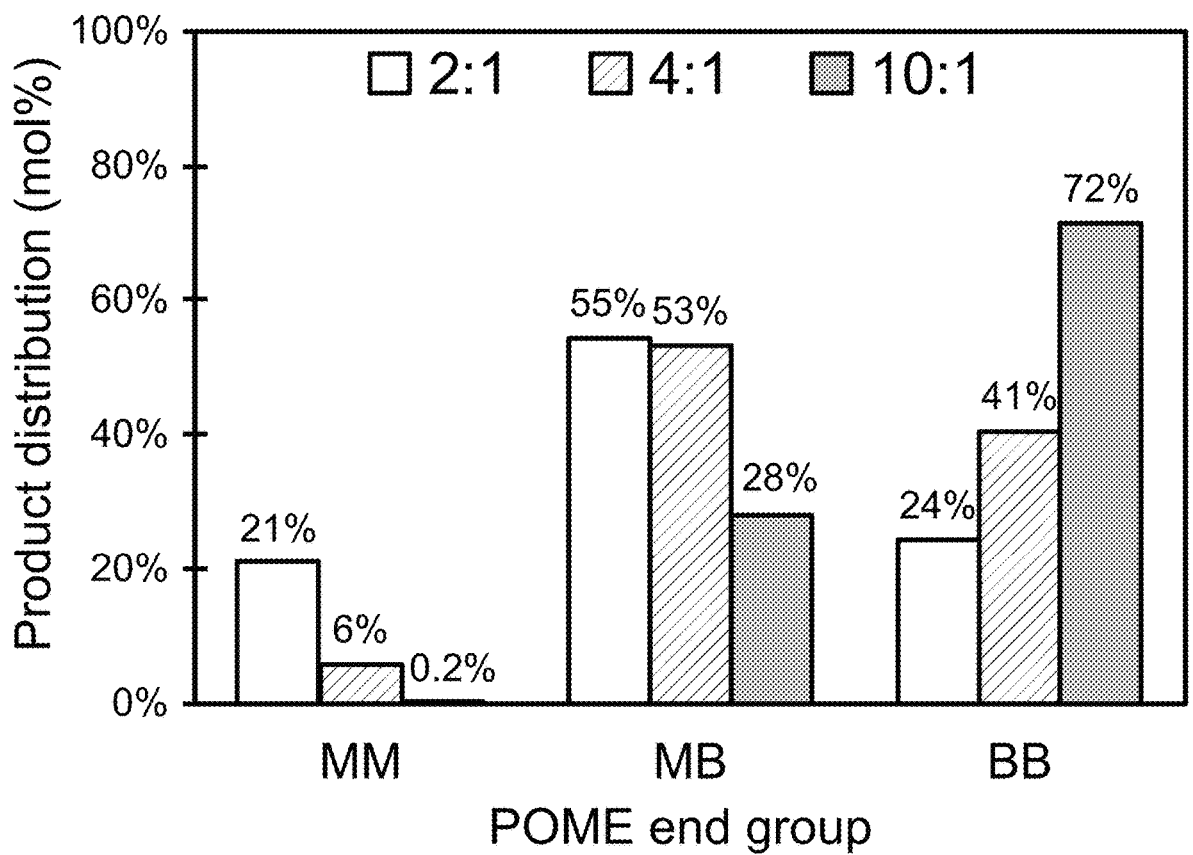
FIG. 2A illustrates calculated equilibrium product distributions of exchanged end-groups for catalytic end-group exchange reactions with 2:1, 4:1, and 10:1 BuOH:MM-$POME_{3-6}$ molar ratios (determined using Aspen Plus), according to some embodiments of the present disclosure. Simulated conditions: Isothermal at 60° C. and atmospheric pressure (in Golden, CO=82.2 kPa) assuming an ideal system in liquid-phase. Detailed product distributions are summarized in Table 2.
Figure 2B:
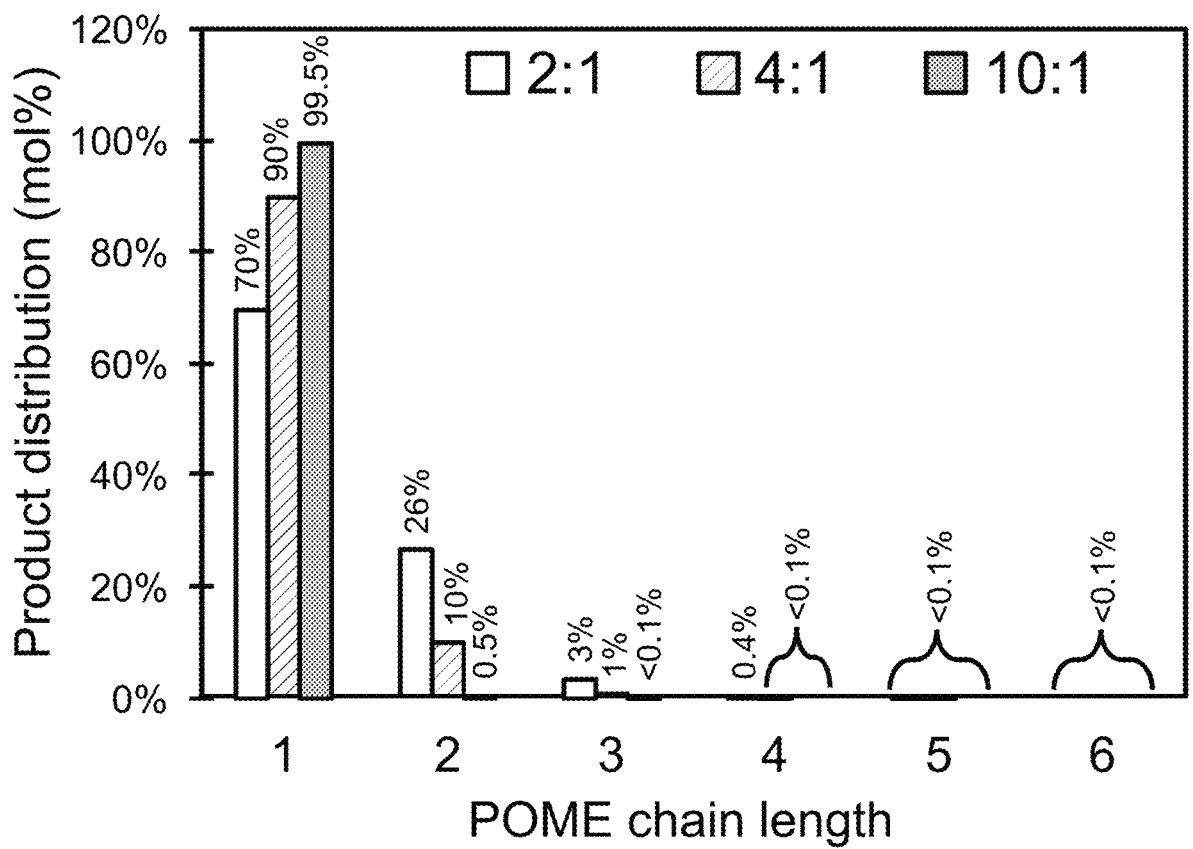
FIG. 2B illustrates calculated equilibrium product distributions of POME chain length for catalytic end-group exchange reactions with 2:1, 4:1, and 10:1 BuOH:MM-$POME_{3-6}$ molar ratios (determined using Aspen Plus), according to some embodiments of the present disclosure. Simulated conditions: Isothermal at 60° C. and atmospheric pressure (in Golden, CO=82.2 kPa) assuming an ideal system in liquid-phase. Detailed product distributions are summarized in Table 2.
Figure 3A:
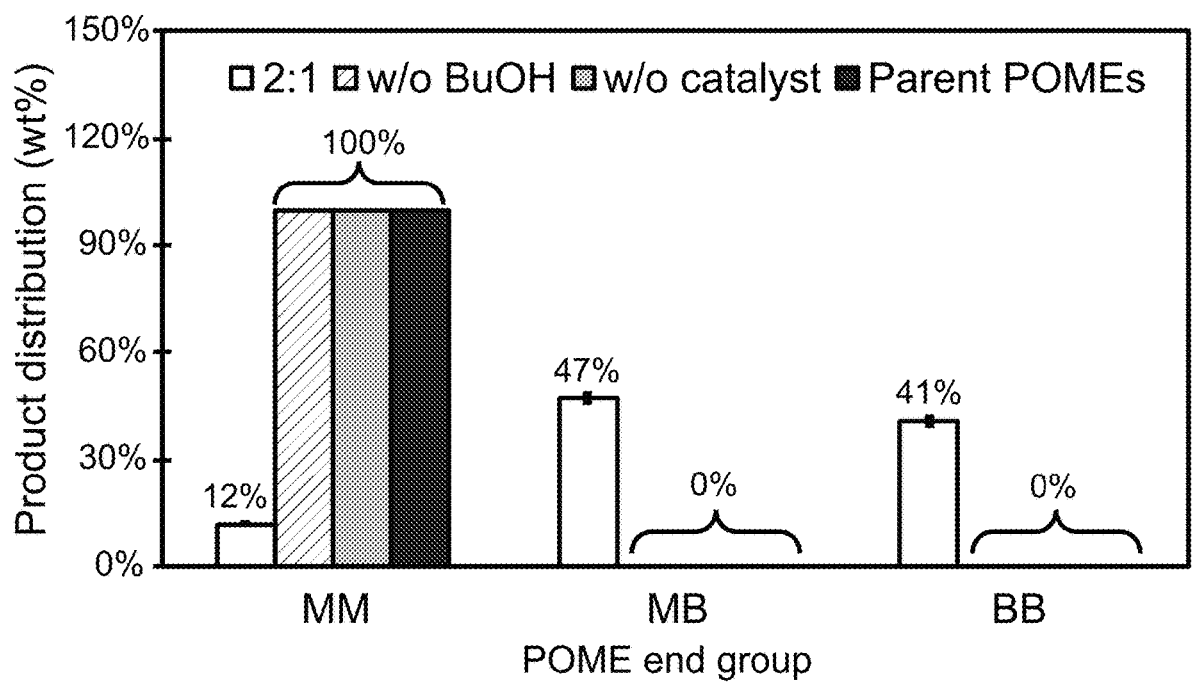
FIGS. 3A, 3B, and 3C illustrate results from control experiments for the end-group exchange reaction, according to some embodiments of the present disclosure. "w/o n-BuOH" denotes the reaction of MM-$POME_{3-6}$ with catalyst but without n-BuOH; "w/o catalyst" denotes the reaction with a 2:1 n-BuOH:MM-$POME_{3-6}$ mol ratio but without catalyst. Product distribution of (FIG. 3A) POME end-groups, (FIG. 3B) POME chain length and (FIG. 3C) POME end-groups in the desired boiling point range. MM-POME$_{3-6}$ composition included for reference (Parent POMEs).
Figure 3B:
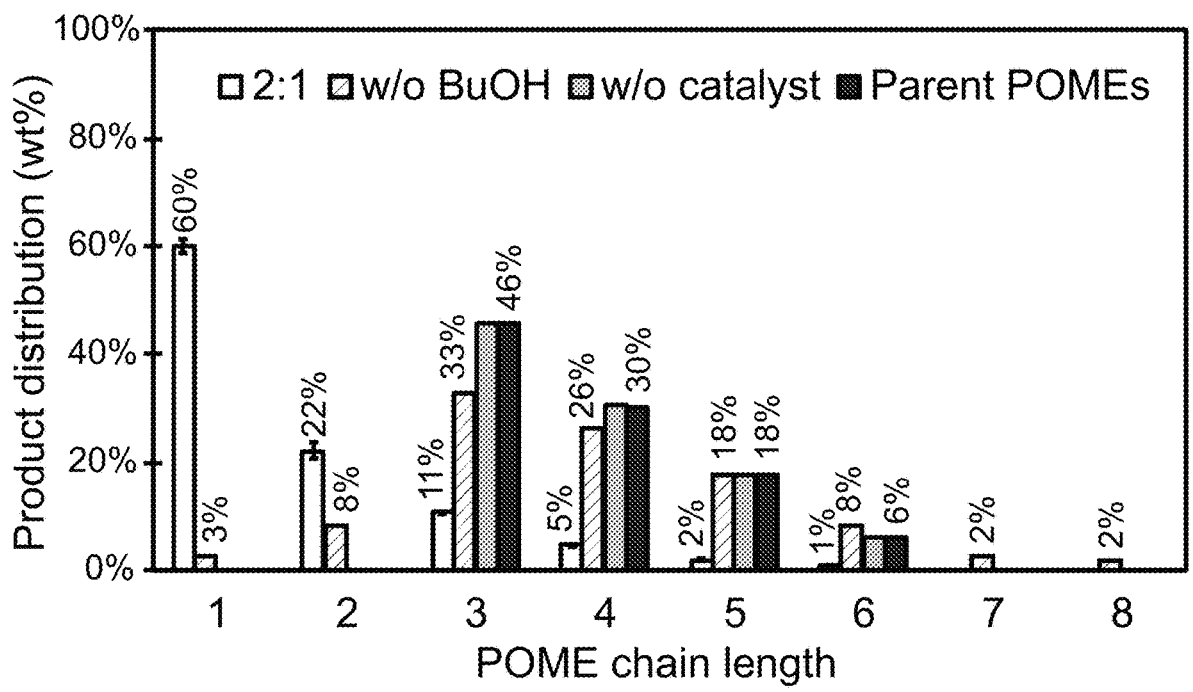
Figure 3C:
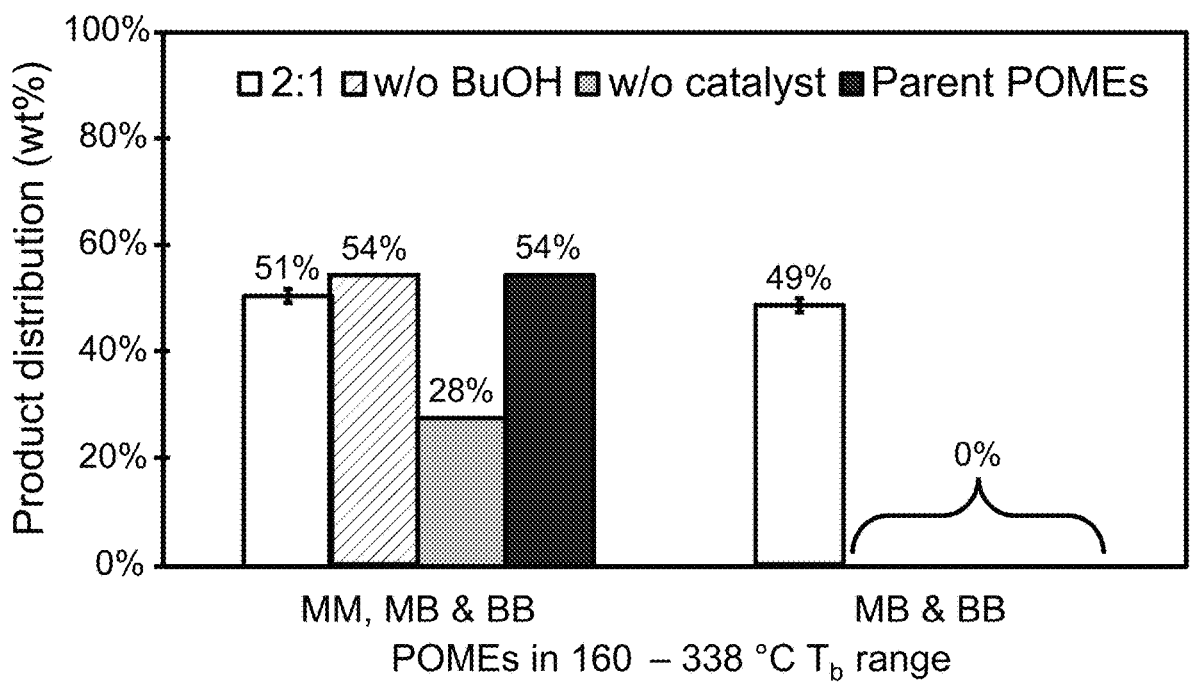

As described herein, in some embodiments of the present disclosure, end-group exchange chemistry via a trans-acetalization reaction was investigated at about 60° C. using an acidic catalyst, Amberlyst-46, which is from a family of sulfonic acid resins that also fall within the scope of the present disclosure. Refer to Scheme 1 below, which illustrates an acid-catalyzed trans-acetalization reaction of BuOH with MM-POME$_{3-6}$ where B and M represent butyl and methyl groups, respectively. Scheme 1 also shows the minor hemiacetal products in this reaction having one M or B termination and one alcohol termination, denoted with H). For clarity, the nomenclature MM-POME$_{3-6}$ refers to a mixture of POMEs molecules having between 3 and 6 oxymethylene repeat units, where each molecule is end-capped on both ends with a methyl group (—CH$_3$). The thermodynamic limit for the trans-acetalization reaction was calculated assuming system ideality to enable a comparison of experimentally observed product selectivity for both end-group exchange and chain length. Detailed Aspen Plus calculation results are presented in FIGS. 2A and 2B and Table 2. Control experiments of the parent MM-POME$_{3-6}$ mixture and BuOH without the acid catalyst, or in the presence of catalyst but without BuOH, exhibited no exchange of the methyl end-groups of the parent MM-POMEs (see FIGS. 3A, 3B, and 3C and Table 3).

Scheme 1

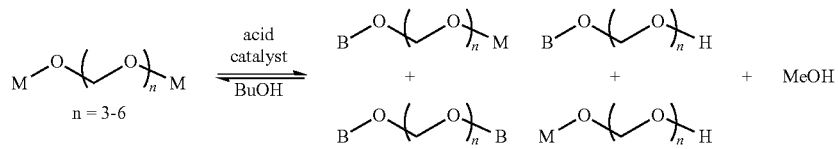

TABLE 2

Experimental and calculated equilibrium product distributions for the trans-acetalization reaction with 2:1, 4:1, and 10:1 BuOH:MM-POME$_{3-6}$ molar ratios. Calculated values obtained using Aspen Plus. Simulated reaction conditions: Isothermal at 60° C. and atmospheric pressure (in Golden, CO = 82.2 kPa) assuming an ideal system in liquid-phase. The calculated final product distributions were correlated to products identified from experimental conditions (i.e., excluded water and hemiacetals that were not observed). Methanol (MeOH) and formaldehyde (FA) are grouped in this analysis due to peak overlap.

| | 2:1 | | 4:1 | | 10:1 | |
|---|---|---|---|---|---|---|
| ID | Exp. mol % | Calc. mol % | Exp. mol % | Calc. mol % | Exp. mol % | Calc. mol % |
| MeOH + FA | 33 | 34 | 14 | 17 | <0.1 | 1.6 |
| BuOH | 11 | 3.7 | 23 | 11 | 61 | 45 |
| MM-POME$_1$ | 3.7 | 0.9 | 3.1 | 0.7 | 3.0 | 0.1 |
| MB-POME$_1$ | 19 | 29 | 24 | 36 | 10 | 15 |
| BB-POME$_1$ | 13 | 14 | 29 | 28 | 23 | 38 |
| MM-POME$_2$ | 3.0 | 11 | 0.5 | 3.5 | — | <0.1 |
| MB-POME$_2$ | 5.2 | 4.5 | 2.5 | 2.4 | 0.2 | 0.1 |
| BB-POME$_2$ | 3.7 | 1.4 | 2.3 | 1.2 | 0.3 | 0.1 |
| MM-POME$_3$ | 1.2 | 1.5 | 0.9 | 0.2 | 0.2 | <0.1 |
| MB-POME$_3$ | 2.4 | 0.5 | 0.2 | 0.1 | <0.1 | <0.1 |
| BB-POME$_3$ | 1.2 | 0.1 | 0.2 | <0.1 | — | <0.1 |
| MM-POME$_4$ | 0.6 | 0.2 | 0.8 | <0.1 | 0.2 | <0.1 |
| MB-POME$_4$ | 1.0 | <0.1 | <0.1 | <0.1 | <0.1 | <0.1 |
| BB-POME$_4$ | 0.3 | <0.1 | <0.1 | <0.1 | — | <0.1 |
| MM-POME$_5$ | 0.3 | <0.1 | <0.1 | <0.1 | <0.1 | <0.1 |
| MB-POME$_5$ | 0.2 | <0.1 | <0.1 | <0.1 | <0.1 | <0.1 |
| BB-POME$_5$ | 0.1 | <0.1 | — | <0.1 | — | <0.1 |
| MM-POME$_6$ | 0.1 | <0.1 | 0.2 | <0.1 | 0.1 | <0.1 |
| MB-POME$_6$ | 0.1 | <0.1 | — | <0.1 | — | <0.1 |

TABLE 3

Experimental product distribution of trans-acetalization reactions with 2:1 BuOH:MM-POME$_{3-6}$ molar ratio, and control experiments without BuOH and without catalyst. MM-POME$_{3-6}$ composition added for reference.

| | 2:1 | | w/o BuOH | | w/o catalyst | | MM-POME$_{3-6}$ | |
|---|---|---|---|---|---|---|---|---|
| ID | mol % | wt % | mol % | wt % | mol % | wt % | mol % | wt % |
| MeOH + FA | 33 | 10 | 17 | 4 | — | — | — | — |
| BuOH | 11 | 8.0 | — | — | 67 | 49 | — | — |
| MM-POME$_1$ | 3.7 | 3.2 | 4.2 | 2.4 | — | — | — | — |
| MB-POME$_1$ | 19 | 24 | — | — | — | — | — | — |
| BB-POME$_1$ | 13 | 22 | — | — | — | — | — | — |
| MM-POME$_2$ | 3.0 | 3.0 | 10 | 7.9 | — | — | — | — |
| MB-POME$_2$ | 5.2 | 7.9 | — | — | — | — | — | — |
| BB-POME$_2$ | 3.7 | 7.3 | — | — | — | — | — | — |
| MM-POME$_3$ | 1.2 | 1.6 | 31 | 31 | 17 | 23 | 53 | 46 |
| MB-POME$_3$ | 2.4 | 4.4 | — | — | — | — | — | — |
| BB-POME$_3$ | 1.2 | 2.8 | — | — | — | — | — | — |
| MM-POME$_4$ | 0.6 | 0.9 | 20 | 25 | 9.4 | 15 | 29 | 30 |
| MB-POME$_4$ | 1.0 | 2.0 | — | — | — | — | — | — |
| BB-POME$_4$ | 0.3 | 0.9 | — | — | — | — | — | — |
| MM-POME$_5$ | 0.3 | 0.7 | 11 | 17 | 4.7 | 9.0 | 14 | 18 |
| MB-POME$_5$ | 0.2 | 0.6 | — | — | — | — | — | — |
| BB-POME$_5$ | 0.1 | 0.3 | — | — | — | — | — | — |
| MM-POME$_6$ | 0.1 | 0.3 | 4.6 | 7.8 | 1.4 | 3.0 | 4.2 | 6.1 |
| MB-POME$_6$ | 0.1 | 0.2 | — | — | — | — | — | — |
| BB-POME$_6$ | <0.1 | 0.1 | — | — | — | — | — | — |
| POME$_7$ MM | — | — | 1.2 | 2.4 | — | — | — | — |
| POME$_8$ MM | — | — | 0.7 | 1.5 | — | — | — | — |

Figure 4A:
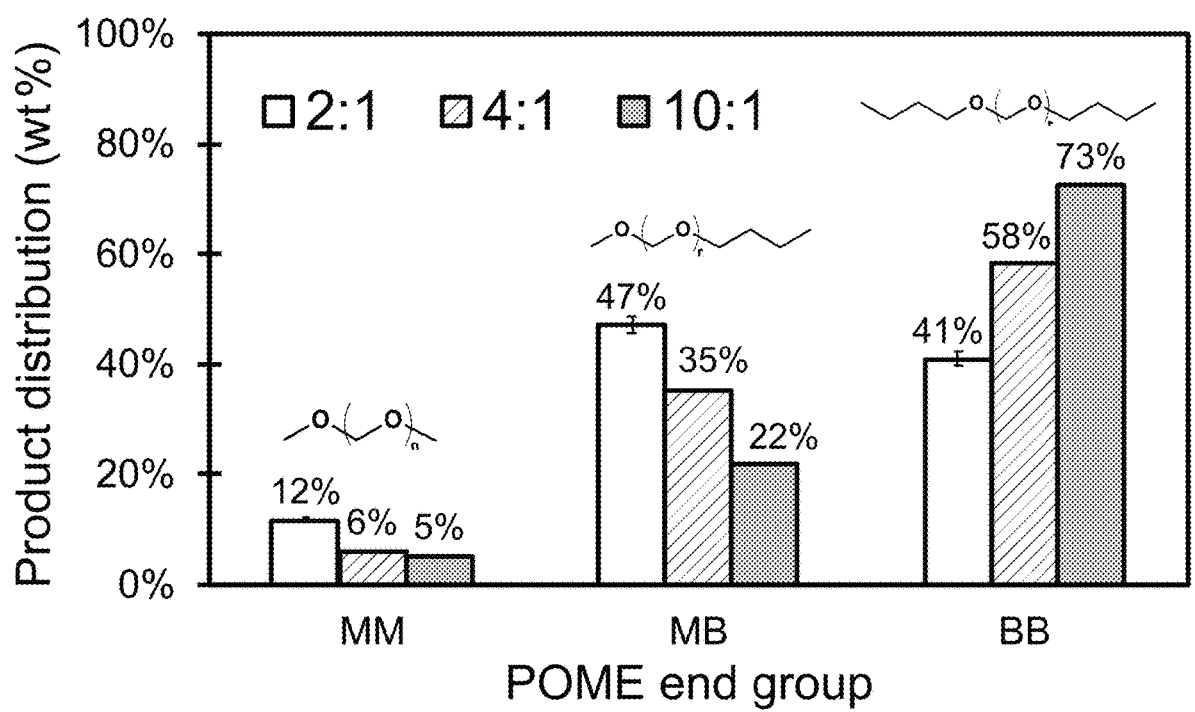
FIG. 4A illustrates product distribution of exchanged end-groups in a desired boiling point range after catalytic end-group exchange reactions with 2:1, 4:1, and 10:1 n-BuOH:MM-POME$_{3-6}$ molar ratios, according to some embodiments of the present disclosure. Detailed product distributions are summarized in Table 15. Standard error bars are included for the 2:1 n-BuOH:MM-POME$_{3-6}$ molar ratio condition.
Figure 5:
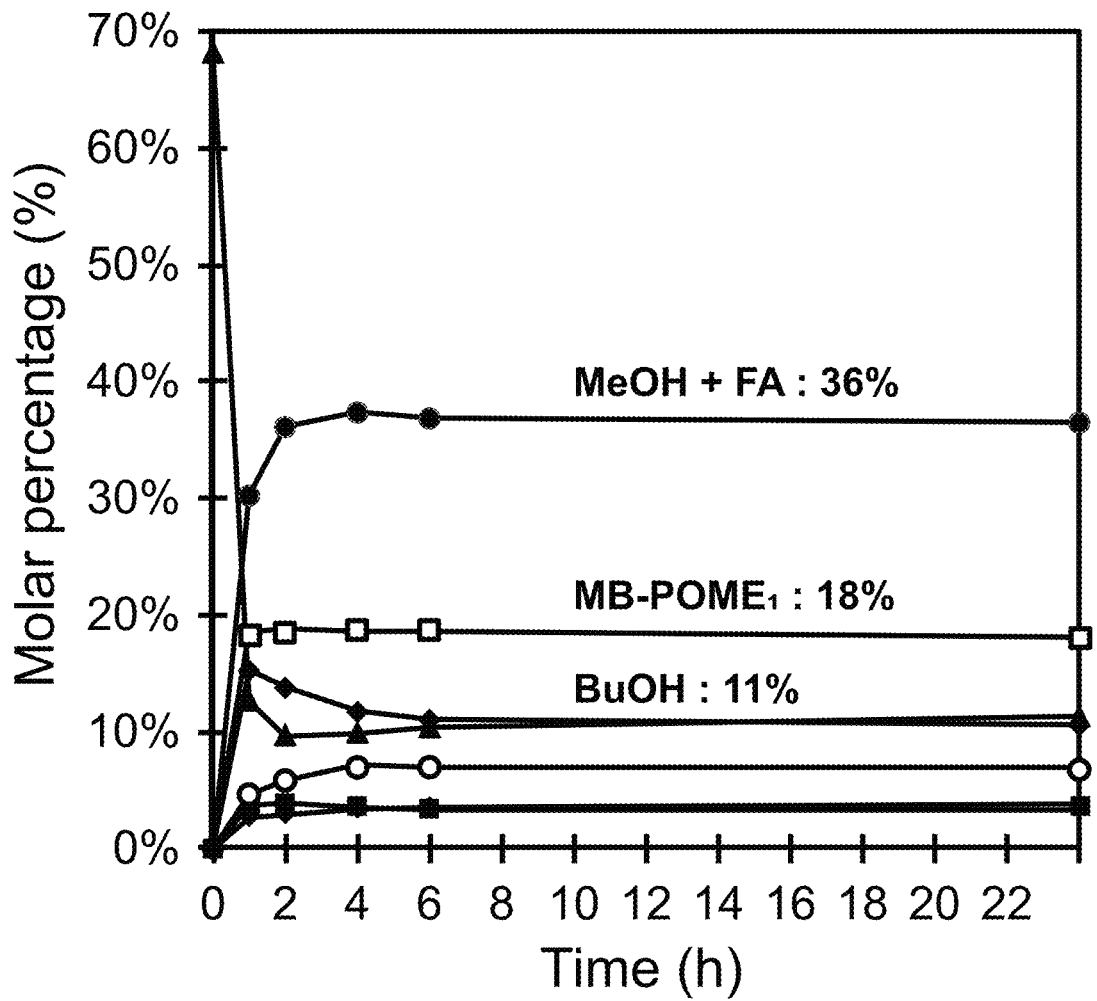
FIG. 5 illustrates product distribution from catalytic end-group exchange with 2:1 n-BuOH:MM-POME$_{3-6}$ molar ratio over 24 hours of reaction, according to some embodiments of the present disclosure. Results are summarized in Table 4.
Figure 6A:
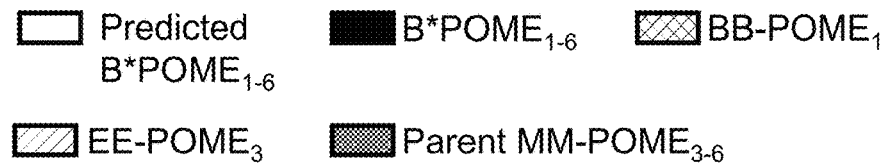
FIGS. 6A and 6B illustrate plots of measured Tier 1 fuel properties for B*POME$_{1-6}$ compared to predicted fuel properties assuming linear blending, and measured fuel properties for MM-POME$_{3-6}$, n-BB-POME$_1$, and EE-POME$_3$, according to some embodiments of the present disclosure. Details of linear blending analysis are summarized in Table 13. The targeted region for each fuel property is indicated by the arrow marked with the specific numerical criterion for diesel blend stocks.
Figure 6A:
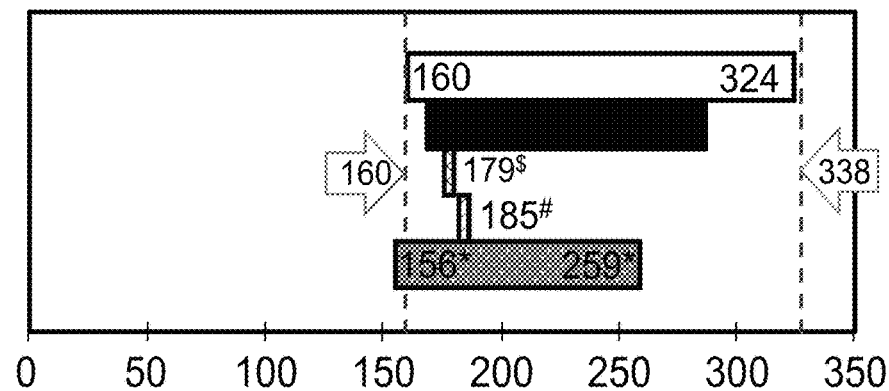
Figure 6A:
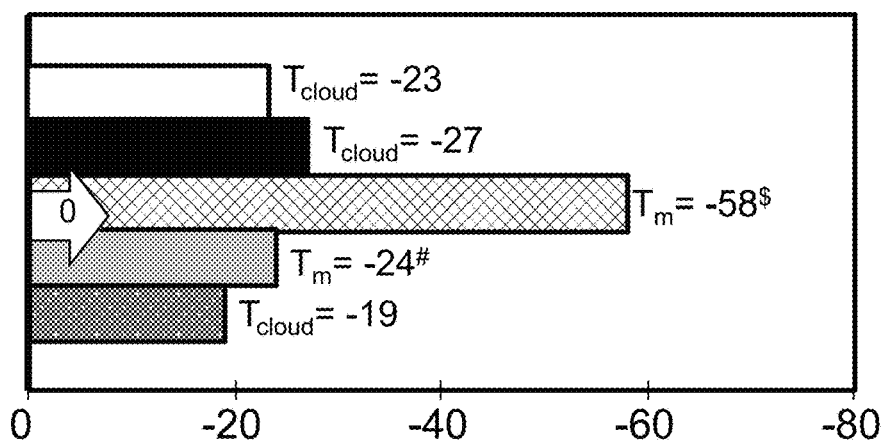
Figure 6A:
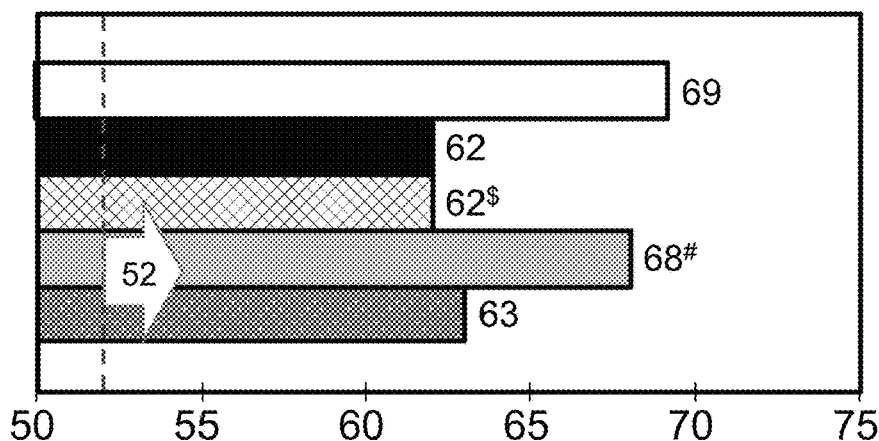
Figure 6B:
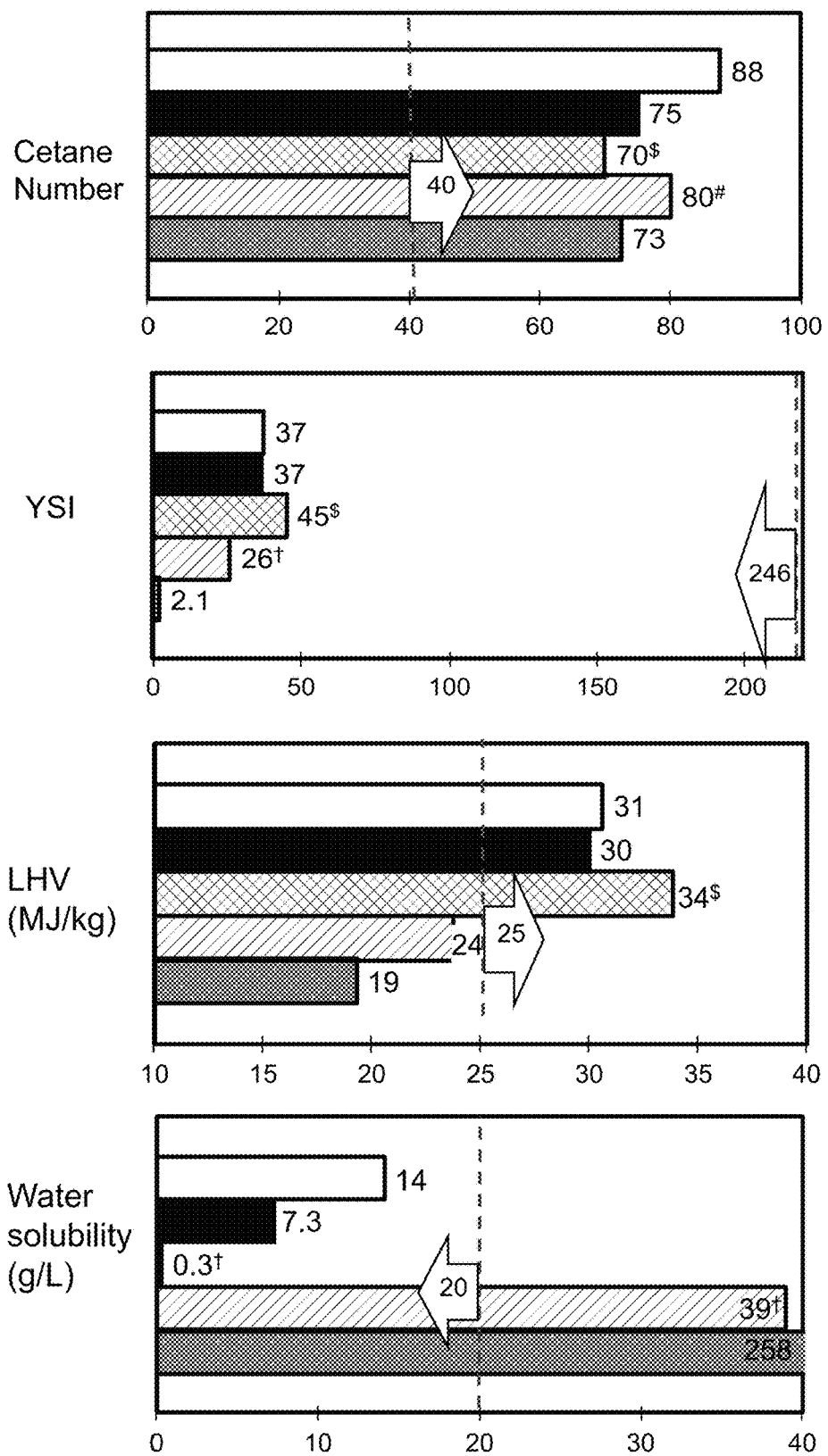

FIG. 4A presents the product distribution from the trans-acetalization of the parent MM-POME$_{3-6}$ into BB-POME$_n$ and a mixed end-group MB-POME$_n$ product (i.e., single exchange giving methyl-butyl end-groups) at 60° C. and atmospheric pressure over 4.6 wt % of Amberlyst-46 for a reaction time of about 4 hours. With a stoichiometric molar ratio of about 2:1 for BuOH:MM-POME$_{3-6}$, substantial butyl exchange was observed, yielding about 47 wt % of the single-exchanged and about 41 wt % double-exchanged products. After about 4 hours under these conditions, the products reached near-equilibrium concentrations (see FIG. 5 and Table 4; unlabeled data sets correspond to: solid triangles—BB-POME$_1$:11%; empty circles—MB-POME$_2$: 6.7%; solid squares—BB-POME$_2$:3.9%; and solid diamonds—MM-POME$_1$:3.6%).

TABLE 4

Detailed molar fraction of trans-acetalization products over time. Trans-acetalization with a 2:1 BuOH:MM-POME$_{3-6}$ molar ratio. Methanol (MeOH) and formaldehyde (FA) are grouped in this analysis due to peak overlap.

| ID | 0 h mol % | 1 h mol % | 2 h mol % | 4 h mol % | 6 h mol % | 24 h mol % |
|---|---|---|---|---|---|---|
| MeOH + FA | — | 30 | 36 | 37 | 37 | 36 |
| BuOH | 68.1 | 13 | 9.6 | 9.8 | 10 | 11 |
| MM-POME$_1$ | — | 3.7 | 3.9 | 3.5 | 3.4 | 3.6 |
| MB-POME$_1$ | — | 18 | 19 | 19 | 19 | 18 |
| BB-POME$_1$ | — | 15 | 14 | 12 | 11 | 11 |
| MM-POME$_2$ | — | 1.6 | 2.6 | 2.0 | 2.2 | 2.5 |
| MB-POME$_2$ | — | 4.6 | 5.8 | 6.9 | 7.0 | 6.7 |
| BB-POME$_2$ | — | 2.7 | 2.9 | 3.4 | 3.6 | 3.9 |

TABLE 4-continued

Detailed molar fraction of trans-acetalization products over time. Trans-acetalization with a 2:1 BuOH:MM-POME$_{3-6}$ molar ratio. Methanol (MeOH) and formaldehyde (FA) are grouped in this analysis due to peak overlap.

| ID | 0 h mol % | 1 h mol % | 2 h mol % | 4 h mol % | 6 h mol % | 24 h mol % |
|---|---|---|---|---|---|---|
| MM-POME$_3$ | 18.1 | 4.4 | 1.7 | 1.1 | 1.1 | 0.8 |
| MB-POME$_3$ | — | 0.9 | 1.6 | 2.3 | 2.4 | 2.3 |
| BB-POME$_3$ | — | 0.4 | 0.6 | 1.0 | 1.2 | 1.4 |
| MM-POME$_4$ | 9.9 | 3.1 | 1.3 | 0.7 | 0.6 | 0.5 |
| MB-POME$_4$ | — | 0.2 | 0.5 | 0.8 | 1.0 | 1.0 |
| BB-POME$_4$ | — | <0.1 | 0.1 | 0.2 | 0.3 | 0.4 |
| MM-POME$_5$ | 3.7 | 1.6 | 0.8 | 0.3 | 0.3 | 0.2 |
| MB-POME$_5$ | — | <0.1 | <0.1 | 0.1 | 0.1 | 0.2 |
| MM-POME$_6$ | 0.3 | 0.3 | 0.1 | 0.1 | <0.1 | <0.1 |

These initial results demonstrated a simple route to incorporate higher alcohols into the POME structures under mild reaction conditions. It is also important to note that the acidic ion-exchange resin catalyst, e.g., Amberlyst-46, was used for the end-group exchange reaction, and the reaction did not occur at the studied conditions without catalyst, although it is anticipated that other solid acid catalysts can also catalyze these reactions (see FIGS. 3A, 3B, and 3C and Table 3 above). Reactions with excess BuOH were investigated with two additional molar ratios of 4:1 and 10:1 for BuOH:MM-POME$_{3-6}$. With excess BuOH, dibutyl-exchange to yield BB-POME$_n$ increased with a concomitant decrease in single-exchanged MB products, with the 4:1 ratio yielding 58 wt % BB products and the 10:1 ratio yielding 73 wt % BB products. These results are in agreement with the predicted thermodynamic limitations of the exchange chemistry that indicate increased exchange of MM-POME$_n$ end-groups with increasing initial ratios of BuOH:MM-POME$_{3-6}$ (see FIGS. 2A and 2B and Table 2 above). A portion of the MM-POME$_{3-6}$ starting material remained even when excess alcohol was used (12 wt %, 6 wt % and 5 wt % for the 2:1, 4:1 and 10:1 ratio respectively, see FIG. 4A), in line with the thermodynamic limitations (see FIGS. 2A and 2B). Although all of these reactions were performed using the mixture of POMEs, MM-POME$_{3-6}$, as shown in the last column of Table 3 above, this mixture was used to enable demonstration of the concepts described herein and are not intended to be limiting. The end-group exchange reactions described herein apply to other mixtures of starting POMEs molecules, with different lengths, different compositions, and different concentrations. All of the possible combinations of chain length, type of end-groups, and concentrations are considered within the scope of the present disclosure.

Figure 4B:
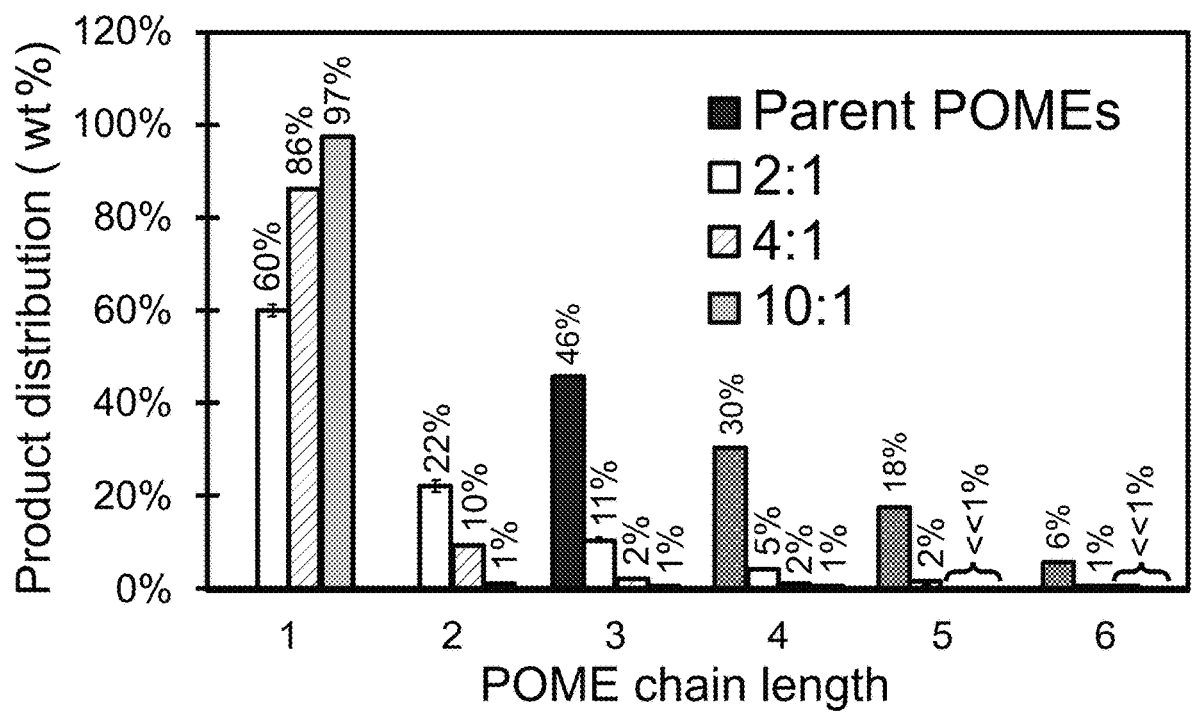
FIG. 4B illustrates product distribution of POME chain length in a desired boiling point range after catalytic end-group exchange reactions with 2:1, 4:1, and 10:1 n-BuOH: MM-POME$_{3-6}$ molar ratios, according to some embodiments of the present disclosure. Chain length distribution for the parent MM-POME$_{3-6}$ is shown for reference. Detailed product distributions are summarized in Table 15. Standard error bars are included for the 2:1 n-BuOH:MM-POME$_{3-6}$ molar ratio condition.

During the end-group exchange reaction, the chain lengths redistributed to a range of n=1-6, with n=1 being most abundant at 60 wt % for the 2:1 ratio of starting reactants (see FIG. 4B), 86 wt % for the 4:1 ratio and up to 97 wt % for the 10:1 ratio. Thermodynamic calculations for the trans-acetalization reaction indicate that the breakdown of longer MM-POMEs with n=3-6 into shorter chains with n=1-2 is energetically favored ($K_{eq}$=102, Reaction Numbers 15-18, 20-24 in Table 5). As outlined by the computational analysis, the BB end-groups offset the detrimental effect of chain shortening by shifting the fuel properties of n=1-2 POMEs into the desired, advantageous range. The control experiment without BuOH demonstrated that the parent POMEs undergo a redistribution of chain lengths with Amberlyst-46, giving a distribution in the range of n=1-8 with n=3 being most abundant at 33 wt % (see FIG. 3). The control experiment without catalyst confirmed that no end-group exchange chemistry occurred in the absence of catalyst, and further, the chain lengths were not redistributed.

TABLE 5

Calculated thermodynamic equilibrium constant ($K_{eq}$) using Aspen Plus for the trans-acetalization reaction with 2:1 BuOH:MM-POME$_{3-6}$ molar ratio. Simulated reaction conditions: Isothermal at 60° C. and atmospheric pressure (in Golden, CO = 82.2 kPa) assuming an ideal system in liquid-phase.

| Reaction | Stoichiometry | Equilibrium constant ($K_{eq}$) |
|---|---|---|
| 1 | MM-POME$_1$ + 2 BuOH → BB-POME$_1$ + 2 METHANOL | 9.66E−04 |
| 2 | MM-POME$_2$ + 2 BuOH → BB-POME$_2$ + 2 METHANOL | 1.73E−05 |
| 3 | MM-POME$_3$ + 2 BuOH → BB-POME$_3$ + 2 METHANOL | 1.73E−05 |
| 4 | MM-POME$_4$ + 2 BuOH → BB-POME$_4$ + 2 METHANOL | 1.73E−05 |
| 5 | MM-POME$_5$ + 2 BuOH → BB-POME$_5$ + 2 METHANOL | 1.73E−05 |
| 6 | MM-POME$_6$ + 2 BuOH → BB-POME$_6$ + 2 METHANOL | 1.73E−05 |
| 7 | MM-POME$_1$ + BuOH → MB-POME$_1$ + METHANOL | 2.32E−01 |
| 8 | MM-POME$_2$ + BuOH → MB-POME$_2$ + METHANOL | 4.17E−03 |
| 9 | MM-POME$_3$ + BuOH → MB-POME$_3$ + METHANOL | 4.17E−03 |
| 10 | MM-POME$_4$ + BuOH → MB-POME$_4$ + METHANOL | 4.17E−03 |
| 11 | MM-POME$_5$ + BuOH → MB-POME$_5$ + METHANOL | 4.17E−03 |
| 12 | MM-POME$_6$ + BuOH → MB-POME$_6$ + METHANOL | 4.17E−03 |
| 13 | MM-POME$_1$ → DME + FA | 1.30E−01 |
| 14 | MM-POME$_2$ → POME$_1$MM + FA | 1.84 |
| 15 | MM-POME$_3$ → MM-POME$_2$ + FA | 102.32 |
| 16 | MM-POME$_4$ → MM-POME$_3$ + FA | 102.32 |
| 17 | MM-POME$_5$ → MM-POME$_4$ + FA | 102.32 |
| 18 | MM-POME$_6$ → MM-POME$_5$ + FA | 102.32 |
| 19 | MB-POME$_1$ → MBE + FA | 6.98E−01 |
| 20 | MB-POME$_2$ → MB-POME$_1$ + FA | 102.32 |
| 21 | MB-POME$_3$ → MB-POME$_2$ + FA | 102.32 |
| 22 | MB-POME$_4$ → MB-POME$_3$ + FA | 102.32 |
| 23 | MB-POME$_5$ → MB-POME$_4$ + FA | 102.32 |
| 24 | MB-POME$_6$ → MB-POME$_5$ + FA | 102.32 |
| 25 | MM-POME$_1$ + H$_2$O → FA + 2 METHANOL | 4.19E−04 |
| 26 | MM-POME$_2$ + H$_2$O → HA$_2$ + METHANOL | 6.87E−05 |

TABLE 5-continued

Calculated thermodynamic equilibrium constant ($K_{eq}$) using Aspen Plus for the trans-acetalization reaction with 2:1 BuOH:MM-POME$_{3-6}$ molar ratio. Simulated reaction conditions: Isothermal at 60° C. and atmospheric pressure (in Golden, CO = 82.2 kPa) assuming an ideal system in liquid-phase.

| Reaction | Stoichiometry | Equilibrium constant ($K_{eq}$) |
|---|---|---|
| 27 | MM-POME$_3$ + H$_2$O → HA$_3$ + METHANOL | 6.87E−05 |
| 28 | MM-POME$_4$ + H$_2$O → HA$_4$ + METHANOL | 6.87E−05 |
| 29 | MM-POME$_5$ + H$_2$O → HA$_5$ + METHANOL | 6.87E−05 |
| 30 | MM-POME$_6$ + H$_2$O → HA$_6$ + METHANOL | 6.87E−05 |
| 31 | HA$_1$ + BuOH → MB-POME$_1$ + H$_2$O | 60.61 |
| 32 | HA$_2$ + BuOH → MB-POME$_2$ + H$_2$O | 60.61 |
| 33 | HA$_3$ + BuOH → MB-POME$_3$ + H$_2$O | 60.61 |
| 34 | HA$_4$ + BuOH → MB-POME$_4$ + H$_2$O | 60.61 |
| 35 | HA$_3$ + BuOH → MB-POME$_3$ + H$_2$O | 60.61 |
| 36 | HA$_6$ + BuOH → MB-POME$_6$ + H$_2$O | 60.61 |

Figure 4C:
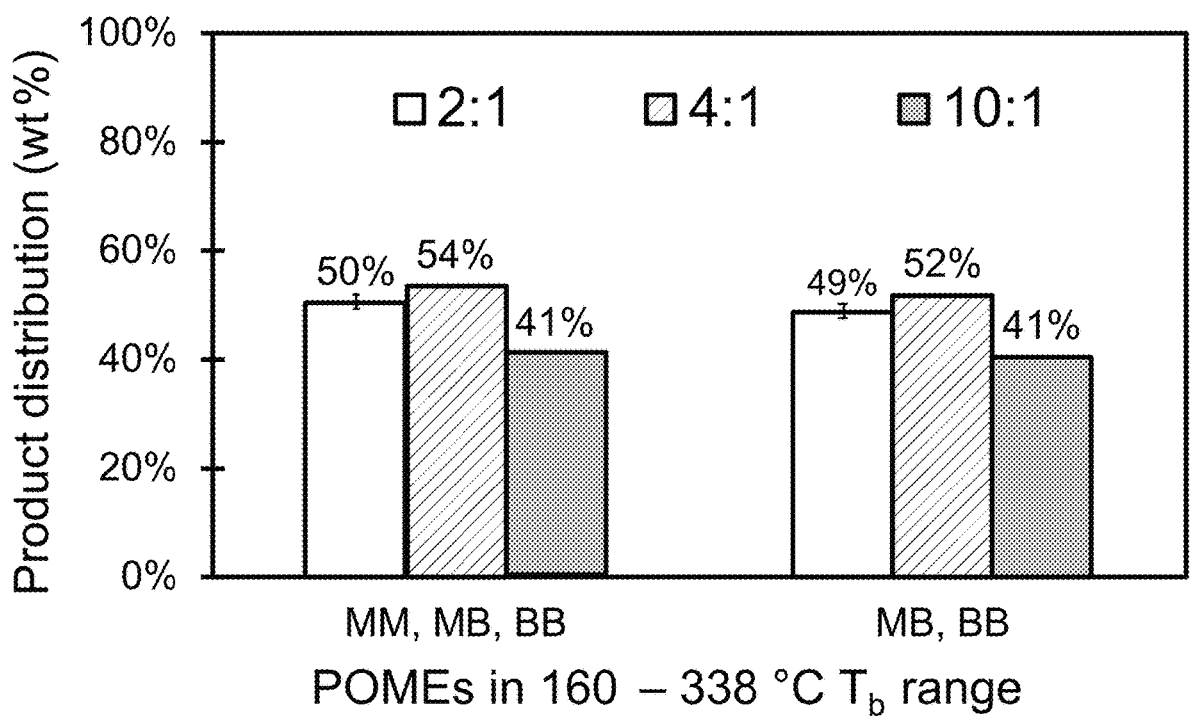
FIG. 4C illustrates fraction of product in a desired boiling point range after catalytic end-group exchange reactions with 2:1, 4:1, and 10:1 n-BuOH:MM-POME$_{3-6}$ molar ratios, according to some embodiments of the present disclosure. Detailed product distributions are summarized in Table 15. Standard error bars are included for the 2:1 n-BuOH:MM-POME$_{3-6}$ molar ratio condition.

HA n = hemiacetal of chemical formula CH$_3$(OCH$_2$)nOH, DME =dimethyl ether, MBE = methyl butyl ether, FA = formaldehyde The crude product mixture of butyl-terminated POMEs contains undesirable light components, such as MeOH and unreacted BuOH, that lie outside of the desired boiling point range (between about 160° C. and about 338° C.). The portion of the crude product that lies within the desired boiling point range is presented in FIG. 4C in two groups: all combinations of end-groups in the target Tb range (i.e., MM, MB, BB), and only the butyl-terminated (MB, BB) species. The reaction with a 2:1 BuOH:MM-POME$_{3-6}$ ratio yielded about 50 wt % of the total products in the desired boiling point range, with about 49 wt % corresponding to butyl-terminated POMEs. With an initial BuOH:MM-POME$_{3-6}$ ratio of 4:1, a comparable portion of the product distribution was in the desired boiling point range, about 54 wt %, with about 52 wt % corresponding to butyl-terminated POMEs. Increasing the initial BuOH:MM-POME$_{3-6}$ ratio to 10:1 promoted the double end-group exchange reaction, however, the excess BuOH diluted the composition, resulting in a lower fraction of the crude product mixture in the desired boiling point range (~41 wt %). Finally, it is worth noting that for the 2:1 and 4:1 molar ratios, 97-98 wt % of the products in the desired boiling point range corresponded to butyl-terminated POMEs, which are the target products with enhanced fuel properties identified from the computational analysis. The 2:1 molar ratio was chosen to prepare a large batch of butyl-exchanged product, due to the combination of an adequate end-group exchange yield in the desired distillate boiling range (~49 wt %) and the minimum volume of BuOH to be separated from the product.

Separation of Desired Products.

Distillation of the butyl-terminated POME product mixture was performed, targeting a product in the boiling point range between about 160° C. and about 338° C. To reduce the presence of reactive light species in the product (e.g., residual formaldehyde, MeOH, DMM, BuOH) during distillation, the crude product was washed with a carbonate-buffered aqueous solution (pH=~9.2) followed by a vacuum treatment at about 50° C. and about 50 mbar. This treatment of the butyl-terminated POME product resulted in a decrease of light species from 21 wt % to 5 wt % of total mass (see Table 6 below). The washed product was readily separated in a spinning band distillation column to yield approximately 100 mL of the targeted MB- and BB-terminated POME product in the targeted boiling point range between about 160° C. and about 338° C. This distilled product is referred to as B*POME$_{1-6}$. As presented in Table 6, 46 wt % of B*POME$_{1-6}$ corresponds to the major product from the reaction, BB-POME$_1$ (or butylal).

TABLE 6

Mass composition of mixed POME product from the end-group exchange reaction with a 2:1 BuOH:MM-POME$_{3-6}$ molar ratio, composition after removal of light products, and the composition of the distilled B*POME$_{1-6}$ product.

| ID | $T_b$ (° C.) | 2:1 BuOH:POME wt % | After 3X Wash + RotoVap wt % | Light products $T_b$ < 160° C. wt % | Desired products $T_b$ 160-338° C. (B*POME$_{1-6}$) mol % | Desired products $T_b$ 160-338° C. (B*POME$_{1-6}$) wt % |
|---|---|---|---|---|---|---|
| MeOH + FA | — | 10 | 1.2 | <0.1 | — | — |
| BuOH | 117.8 | 8.0 | 4.1 | 6.5 | 0.1 | <0.1 |
| MM-POME$_1$ | 42 | 3.2 | <0.1 | — | — | — |
| MB-POME$_1$ | 120-140 | 24 | 26 | 79 | — | — |
| BB-POME$_1$ | 187.2 | 22 | 30 | 4.9 | 48 | 46 |
| MM-POME$_2$ | 99 | 3.0 | 0.4 | — | 0.1 | 0.1 |
| MB-POME$_2$ | 167.1 | 7.9 | 13 | 9.5 | 17 | 14 |
| BB-POME$_2$ | 227.1 | 7.3 | 10 | — | 14 | 16 |
| MM-POME$_3$ | 146 | 1.6 | 0.4 | 0.5 | 0.1 | 0.1 |
| MB-POME$_3$ | — | 4.4 | 5.2 | — | 8.6 | 8.6 |
| BB-POME$_3$ | 263.2 | 2.8 | 3.3 | — | 4.2 | 5.4 |
| MM-POME$_4$ | 189.6 | 0.9 | 0.4 | — | 0.9 | 0.8 |
| MB-POME$_4$ | — | 2.0 | 2.5 | — | 3.3 | 3.9 |

TABLE 6-continued

Mass composition of mixed POME product from the end-group exchange reaction with a 2:1 BuOH:MM-POME$_{3-6}$ molar ratio, composition after removal of light products, and the composition of the distilled B*POME$_{1-6}$ product.

| ID | $T_b$ (° C.) | 2:1 BuOH:POME wt % | After 3X Wash + RotoVap wt % | Light products $T_b$ < 160° C. wt % | Desired products $T_b$ 160-338° C. (B*POME$_{1-6}$) mol % | wt % |
|---|---|---|---|---|---|---|
| BB-POME$_4$ | 295.6 | 0.9 | 1.1 | — | 1.2 | 1.7 |
| MM-POME$_5$ | 242 | 0.7 | 0.3 | — | 0.8 | 0.9 |
| MB-POME$_5$ | — | 0.6 | 0.7 | — | 0.7 | 1.0 |
| BB-POME$_5$ | — | 0.3 | 0.4 | — | 0.5 | 0.8 |
| MM-POME$_6$ | 265.2 | 0.3 | 0.2 | — | 0.2 | 0.3 |
| MB-POME$_6$ | — | 0.2 | 0.2 | — | 0.2 | 0.3 |
| BB-POME$_6$ | — | 0.1 | 1.2 | — | — | — |

Measured Fuel Properties.

The fuel properties of B*POME$_{1-6}$ were measured experimentally and compared to their predicted fuel properties (see FIG. 6). The predicted values were calculated assuming a linear blending of its individual components using the appropriate units for each property (i.e., mol % for CN and YSI; wt % for LHV and water solubility; and vol % for $T_b$, $T_{cloud}$, and $T_{flash}$). The measured properties of B*POME$_{1-6}$ were compared to the Tier 1 criteria and the measured fuel properties of MM-POME$_{3-6}$, BB-POME$_1$, and EE-POME$_3$. All of these POMEs are good reference points to the B*POME$_{1-6}$ product since they encompass a variety of end-groups and chain lengths for comparison of fuel property values.

The B*POME$_{1-6}$ product lies in the target boiling range with a measured T10 and final boiling point between about ° C. 169 and about 287° C. (see Table 7 below). The parent POMEs have a boiling point between about 156° C. and about 259° C., where the lower limit is slightly out of the target (between about 160° C. and about 338° C.). Both BB-POME$_1$ and EE-POME$_3$ are pure components with boiling points of 179° C. and 185° C., respectively. All compared POMEs exceeded the $T_m$ (for pure components) or $T_{cloud}$ (for mixtures) value requirement of less than 0° C. The cloud point of the B*POME$_{1-6}$ was calculated by assuming a linear blending of the predicted melting points ($T_m$) of the pure components in the product. The measured cloud point was −27° C., overpredicted by 4° C. This error is common for melting point calculations. The $T_{flash}$ values were comparable among MM-POME$_{3-6}$ (63° C.), BB-POME$_1$ (62° C.), and B*POME$_{1-6}$ (62° C., overpredicted by 7° C.), with a slightly higher value for EE-POME$_3$ (68° C.), all meeting the required criterion of >52° C.

TABLE 7

Simulated distillation results from thermogravimetric analysis method.

| Sample | T10 (° C.) | T50 (° C.) | T90 (° C.) | FBP (° C.) |
|---|---|---|---|---|
| B*POME$_{1-6}$ | 169 | 207 | 243 | 287 |

The measured cetane number of the B*POME$_{1-6}$ was 75, almost double the minimum requirement (greater than 40). This high cetane value is in a similar range to the comparative POMEs, being slightly greater than the MM-POME$_{3-6}$ (CN=73) and BB-POME$_1$ (70), but slightly lower than EE-POME$_3$ (CN=80). The measured YSI of 37 for B*POME$_{1-6}$ was accurately predicted and is greater than the extremely low value of the MM-POME$_{3-6}$ (YSI=2.1), which is attributed to the absence of C—C bonds in their molecular structure. Considering the mix of methyl and butyl end groups in B*POME$_{1-6}$, the YSI value of 37 between EE-POME$_3$ (predicted YSI=26) and BB-POME$_1$ (YSI=48) follows the same C—C bond reasoning. Despite the increase in YSI for B*POME$_{1-6}$ compared to the starting MM-POME$_{3-6}$, the value lies well below that of a representative certification diesel fuel (less than 246), retaining the advantaged low-sooting properties of POMEs. CN was overpredicted by 17.3%. Computational models for predicting cetane number have been reported with typical errors of +/−10 CNs, and one may associate the high relative error observed for the butyl-terminated product to the unique molecular structure of these POMEs not being adequately represented in the training data set used to develop the prediction models. The measured LHV of 30 MJ/kg for B*POME$_{1-6}$ was in accordance with the predicted linear blending estimate (3.3% error) and exceeded the minimum requirement for this criterion (greater than 25 MJ/kg). This value represents an important improvement to this critical fuel property over the low LHV values of the parent MM-POME$_{3-6}$ (19 MJ/kg) and EE-POME$_3$ (24 MJ/kg), which lie below the Tier 1 target value.

Finally, the B*POME$_{1-6}$ compounds extracted into water were identified and quantified. MM- and MB-POMEs were preferentially extracted into the aqueous layer with BB-POMEs demonstrating low water solubility, as suggested by the computational analysis. For example, MM-POME$_{4-6}$ accounted for 3 g/L, MB-POME$_{2-6}$ for 4 g/L, and BB-POME$_{1-5}$ for only 0.3 g/L. The total water solubility of B*POME$_{1-6}$ was determined to be 7.3 g/L (see Table 8 below). The measured water solubility is a little more than half of the predicted value (14 g/L) and exceeded the target metric (less than 20 g/L). There are still limitations to the modeling methodology to predict fuel properties with new molecular structures, like these MB and BB-terminated POMEs. Water solubility is the metric where B*POME$_{1-6}$ exhibited the greatest advantage when compared to the parent MM-POME$_{3-6}$ (258 g/L) and the EE-POME$_3$ (predicted solubility of 39 g/L), demonstrating a 35-fold and 5-fold reduction respectively.

TABLE 8

Results from water solubility analysis showing product distributions of B*POME$_{1-6}$ in organic and aqueous layers.

| ID | B*POME$_{1-6}$ mol % | Organic layer mol % | Aqueous layer mol % | g/L |
|---|---|---|---|---|
| BuOH | 0.1 | — | 17 | 1.6 |
| BB-POME$_1$ | 48 | 48 | 2.0 | 0.2 |
| MM-POME$_2$ | 0.1 | 0.4 | 5.9 | 0.6 |
| MB-POME$_2$ | 17 | 18 | 25 | 2.4 |
| BB-POME$_2$ | 14 | 14 | 0.8 | 0.1 |
| MM-POME$_3$ | 0.1 | — | — | — |
| MB-POME$_3$ | 8.6 | 8.3 | 12 | 1.1 |
| BB-POME$_3$ | 4.2 | 4.1 | — | — |
| MM-POME$_4$ | 0.9 | 1.1 | 16 | 1.5 |
| MB-POME$_4$ | 3.3 | 3.2 | 3.8 | 0.4 |
| BB-POME$_4$ | 1.2 | 1.1 | — | — |
| MM-POME$_5$ | 0.8 | 0.9 | 11 | 1.1 |
| MB-POME$_5$ | 0.7 | 0.7 | 1.1 | 0.1 |
| BB-POME$_5$ | 0.5 | 0.3 | — | — |
| MM-POME$_6$ | 0.2 | 0.3 | 5.6 | 0.5 |
| MB-POME$_6$ | 0.2 | 0.1 | — | — |
| Total | | | | 9.5 |
| Total w/o BuOH | | | | 7.9 |
| Total MM, MB- and BB-POMEs with $T_b$ > 160° C. (B*POME$_{1-6}$) | | | | 7.3 |
| Total MB- and BB-POMEs with $T_b$ > 160° C. | | | | 4.2 |
| Total BB- POMEs with $T_b$ > 160° C. | | | | 0.3 |

In addition to testing pure POMEs and mixtures of POMEs, POME mixtures resulting from the end-group reactions described above were also tested in blends with a base diesel for a second series of fuel property evaluations, this time Tier 2 properties (see Table 9 below). POME mixtures were blended at about 20 vol % with the base diesel. The Tier 2 properties evaluated included the T90 boiling temperature, viscosity, conductivity, lubricity, cloud point, flash point, CN, oxidation stability, normalized soot concentration (NSC) and LHV of the blend, as these are important performance and safety metrics to consider when introducing a new blend stock to the market. The autoignition properties (i.e., CN) of three different exchanged-POME$_{1-6}$ blend levels (10, 20, and 30 vol %) in a base diesel fuel were measured to determine synergistic and/or antagonistic blending effects.

TABLE 9

Tier 2 criteria for compression ignition (CI) fuel properties.

| Tier 2 fuel property | Criteria Limit |
|---|---|
| Cloud point | <0° C. |
| Oxidation stability (min) | >60 |
| Blend cetane number | ≥40 |
| Viscosity @ 40° C. (cSt) | 1.9 to 4.1 |
| Flash point (° C.) | ≥52 |
| Conductivity (pS/m) | ≥25 |
| Distillation T90 (° C.) | <338 |
| Lubricity @ 60° C. (μm) | ≤520 |
| NSC | <1 |
| LHV(MJ/kg) | >36 |

Figure 7A:
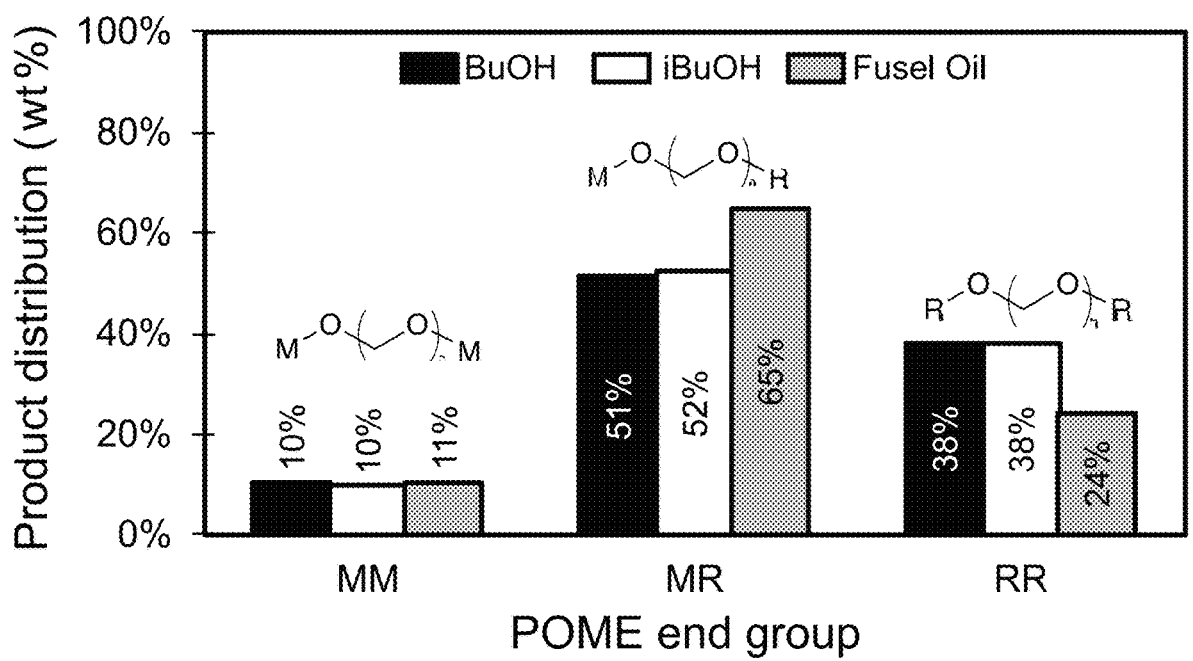
FIGS. 7A and 7B illustrate the elative product distributions of exchanged end-groups (FIG. 7A) POME chain length (FIG. 7B) after catalytic end-group exchange reactions a MM-POME$_{3-6}$ mixture with various alcohols (n-BuOH, iBuOH, and fusel oil), according to some embodiments of the present disclosure.
Figure 7B:
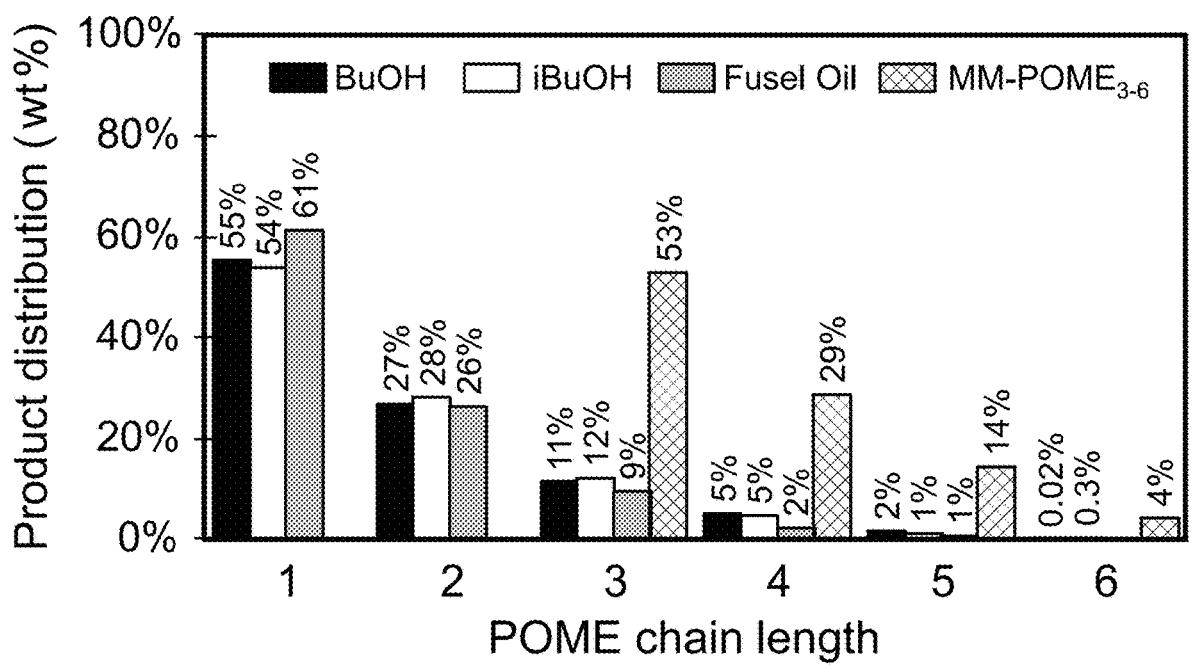

As described above and illustrated in Scheme 1 above, the acid-catalyzed trans-acetalization reaction of different alcohols with the same starting reactant mixture, MM-POME$_{3-6}$, was studied. In this round of experiments, the alcohols studied, R—OH, were 1-butanol, iso-butanol, and fusel oil, where fusel oil is a mixture of alcohols as defined in Table 10 below. The resultant product distributions are illustrated in FIG. 7A. Specifically, FIG. 7A illustrates the distribution of end-groups and FIG. 7B illustrates the distribution of chain lengths, resulting from a starting reactant stoichiometry corresponding to 2:1 molar ratio of R—OH:MM-POME$_{3-6}$, where R—OH=BuOH, iBuOH or fusel oil. The chain length distribution for the parent MM-POME$_{3-6}$ is included in FIG. 7B for reference. The products were analyzed after 17 hours of reaction time and compared to the B*POME$_{1-6}$ product distribution. FIG. 7A presents the product distributions compiled by their end-groups, MM, MR and RR, where M=methyl and in the case of the trans-acetalization with BuOH and iBuOH, R=butyl or isobutyl respectively; in the case of fusel oil, which is a combination of alcohols, R=isobutyl or isopentyl or 2-methyl-1-butyl. Note that for the fusel oil exchanged product, RR represents both a homogeneous and heterogenous end-group combination of the alkyl groups composing the alcohols of the fusel oil. Isobutyl-exchanged POMEs had a similar end-group product distribution as the previously reported butyl-exchanged POMEs, where both had ~10 wt % unreacted MM-POMEs, 51-52 wt % of single-exchanged MR-POMEs, and ~38 wt % double-exchanged RR-POMEs. At an initial 2:1 alcohol:POME molar ratio, these results are consistent with previously reported thermodynamic equilibrium data that suggested single-exchanged MR-POME products are favored. Fusel oil-exchanged POMEs follow a similar trend with unreacted MM-POMEs present at ~11 wt %, single-exchanged MR-POMEs at ~65 wt % and double exchanged RR-POMEs at ~24 wt %.

The product distribution of the crude trans-acetalization POME products compiled by their chain lengths (n=1-6) is presented in FIG. 7B. The parent MM-POME$_{3-6}$ composition is also included as reference. Butyl and isobutyl-exchanged POMEs had a comparable product distribution across chain lengths of n=1-6, but fusel oil-exchanged POMEs were only detected in the n=1-5 range. The crude POME products from all trans-acetalization reactions were redistributed to shorter chain lengths with n=1 being the most abundant (~55 wt %, ~54 wt %, and ~61 wt % for butyl-, isobutyl-, and fusel oil-exchanged POMEs, respectively). As previously reported for the butyl-exchanged POMEs, this redistribution to shorter chain lengths is beneficial to the fuel properties when the longer alkyl groups are added to the molecules.

The crude products of alcohol-exchanged POMEs contain undesirable water-soluble and light components, such as MM-POMEs, formaldehyde, water, hemiacetals (HAs), MeOH and unreacted iBuOH and fusel oil, that lie outside of the desired diesel boiling range (160-338° C.) and water-solubility specifications (less than 20 g/L). To separate the targeted alcohol-exchanged POMEs from the previously described byproducts, the crude products were washed with a carbonate-bicarbonate buffer solution (pH=~9.2) followed by a vacuum treatment at about 50° C. and 50 mbar. The washed products were readily separated in a spinning band distillation column to yield approximately 300 mL of the targeted MR- and RR-terminated POMEs in the 160° C. to 338° C. diesel boiling range. Table 11 summarizes the water-free product distribution of the target product resulting from the reaction of iso-butanol with MM-POME$_{3-6}$, termed iB*POME$_{1-6}$. The water content was 0.063 wt % as measured by Karl-Fischer titration. As described previously, each POME structure is referred to with the abbreviation of each of its end-groups followed by the chain length of the POME in subscript. End group abbreviations are M=methyl and iB=isobutyl. Similarly, Table 12 summarizes the water-free product composition resulting from the reaction of fusel oil with MM-POME$_{3-6}$, termed FOil*POME$_{1-6}$. Water content was ~0.067 wt % as measured by Karl-Fischer titration. As presented in Table 11, ~32.4 wt % of iB*POME$_{1-6}$ corresponded to the major product from the reaction, iBiB-POME$_1$, followed by ~19.5 wt % of iBiB-POME$_2$. The combination of these 2 major components correspond to greater than 50 wt % of the product, which differed from the composition of B*POME$_{1-6}$, where almost 50 wt % of the product corresponded to the BB-POME$_1$ component. Correspondingly, lower concentrations of BB-POME$_{2+}$ chain lengths were present compared to these iBiB-POME analogs. Residual components of MM-POME$_{1-5}$ (~1 wt %) as well as iBuOH (0.2 wt %) were detected in the iB*POME$_{1-6}$ product. The composition of FOil*POME$_{1-5}$ is presented in Table 12. This product is composed of a more complex mixture of POMEs with a variety of end-group combinations, attributed to the complex nature of the initial fusel oil alcohol composition. However, the trend of POME chain length distribution (n=1-5) and end-group exchange (MR- and RR-POMEs) was comparable to the B*POME$_{1-6}$ and iB*POME$_{1-6}$ products. At 27.1, iPM-POME$_2$ is the major component of this product, followed by iPiP-POME$_1$ at ~22.7 wt %. It should be noted that no MM-POME species were detected in the FOil*POME$_{1-5}$ composition, and only ~1 wt % of residual iPeOH was detected in the sample.

TABLE 10

Fusel oil composition

| Component | mol % | wt % |
|---|---|---|
| Iso-butanol (iBuOH) | 9.6 | 8.2 |
| Iso-pentanol (iPeOH) | 80.7 | 81.9 |
| 1-methyl-2-butanol (i.e., sec-butyl carbinol or sBC) | 9.8 | 9.9 |

TABLE 11

Water-free product composition of iB*POME$_{1-6}$.

| | IB*POME$_{1-6}$ | |
|---|---|---|
| ID | mol % | wt % |
| iBuOH | 0.4 | 0.2 |
| MM-POME$_1$ | 0.2 | 0.1 |
| iBM-POME$_1$ | 0.1 | 0.1 |
| iBiB-POME$_1$ | 35.1 | 32.4 |
| MM-POME$_2$ | <0.1 | <0.1 |
| iBM-POME$_2$ | 20.2 | 17.2 |
| iBiB-POME$_2$ | 17.8 | 19.5 |
| MM-POME$_3$ | 0.5 | 0.4 |
| iBM-POME$_3$ | 11.3 | 11.6 |
| iBiB-POME$_3$ | 5.9 | 7.4 |
| MM-POME$_4$ | 0.5 | 0.5 |
| iBM-POME$_4$ | 3.9 | 4.7 |
| iBiB-POME$_4$ | 1.8 | 2.7 |
| iBM-POME$_5$ | 1.3 | 1.7 |
| iBiB-POME$_5$ | 0.6 | 0.9 |
| iBM-POME$_6$ | 0.4 | 0.6 |

TABLE 12

Water-free product composition of FOil*POME$_{1-5}$

| | FOil*POME$_{1-5}$ | |
|---|---|---|
| ID | mol % | wt % |
| iPeOH | 2.1 | 1.0 |
| iBsBC-POME$_1$ | 1.4 | 1.3 |
| iBiP-POME$_1$ | 5.2 | 5.0 |
| iPsBC-POME$_1$ | 2.7 | 2.6 |
| iPiP-POME$_1$ | 22.0 | 22.7 |
| iPM-POME$_2$ | 30.5 | 27.1 |
| sBCM-POME$_2$ | 1.1 | 1.0 |
| iBiP-POME$_2$ | 2.4 | 2.7 |
| iPsBC-POME$_2$ | 0.6 | 0.6 |
| iPiP-POME$_2$ | 9.6 | 11.4 |
| sBCM-POME$_3$ | 0.4 | 0.5 |
| iBM-POME$_3$ | 0.1 | 0.1 |
| iPM-POME$_3$ | 11.6 | 12.2 |
| iPsBC-POME$_3$ | 0.5 | 0.6 |
| iPiP-POME$_3$ | 2.3 | 3.1 |
| iPM-POME$_4$ | 3.2 | 3.8 |
| iBM-POME$_4$ | 0.4 | 0.4 |
| iPiP-POME$_4$ | 0.6 | 0.9 |
| iBM-POME$_5$ | 0.1 | 0.2 |
| iPM-POME$_5$ | 0.7 | 1.0 |

Figure 8A:
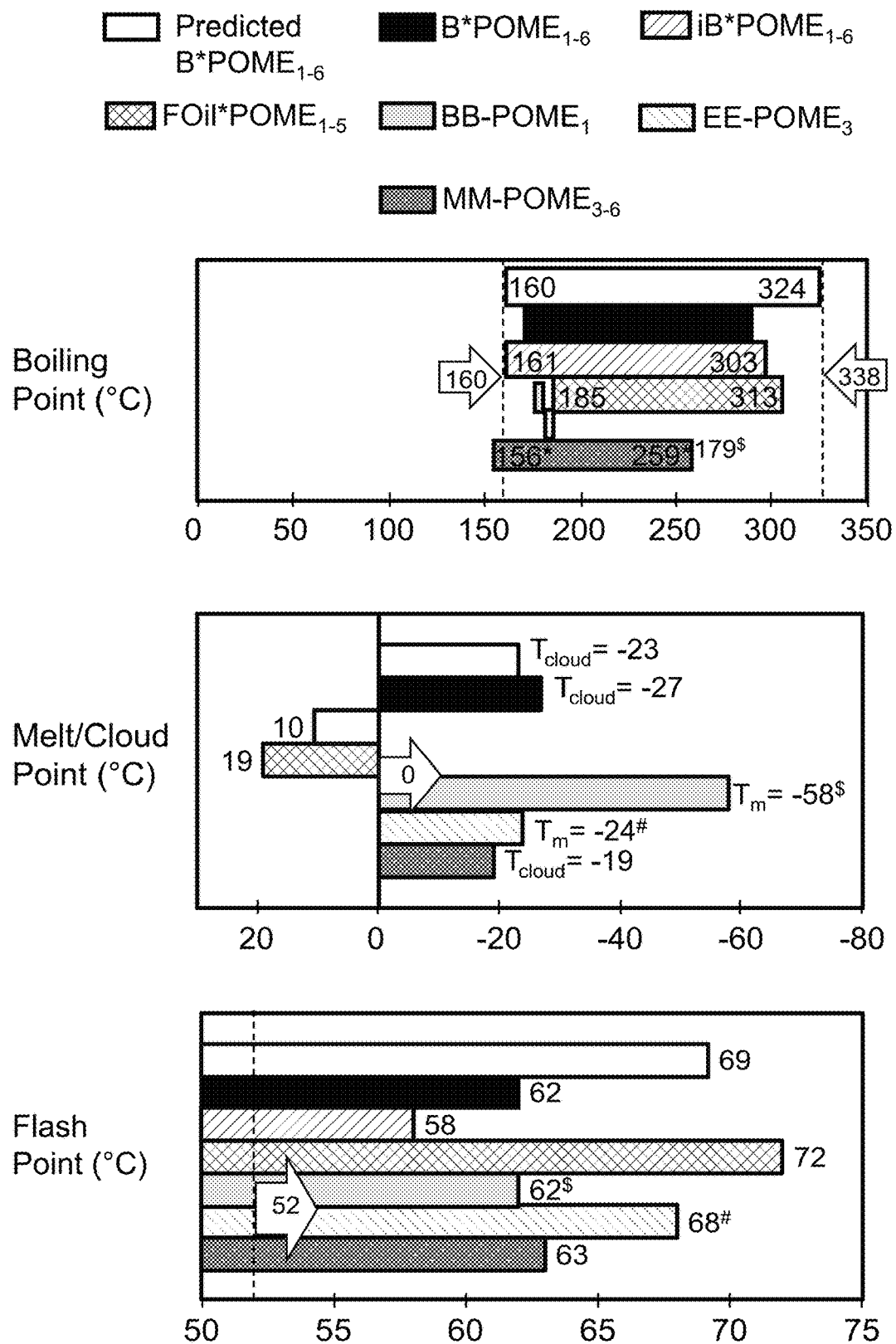
FIGS. 8A and 8B illustrate measured Tier 1 fuel properties for various POME mixtures, according to some embodiments of the present disclosure.
Figure 8B:
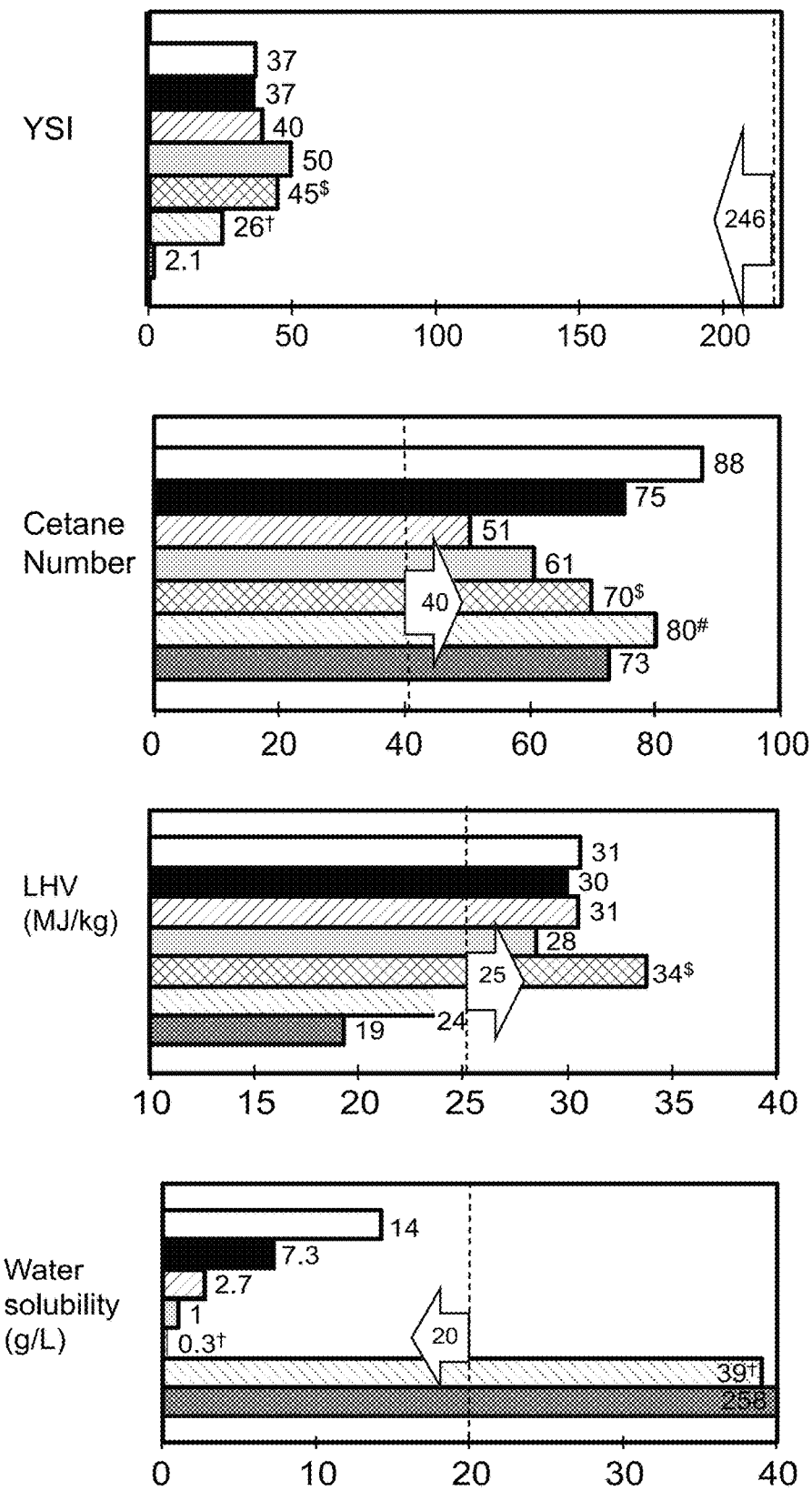

FIGS. 8A and 8B illustrates measured Tier 1 fuel properties for iB*POME$_{1-6}$ and FOil*POME$_{1-5}$ compared to measured fuel properties for B*POME$_{1-6}$ and MM-POME$_{3-6}$ (where B refers to n-butyl end groups). The targeted region for each fuel property is indicated by the arrow marked with the specific numerical criterion for diesel blend stocks.

Figure 9A:
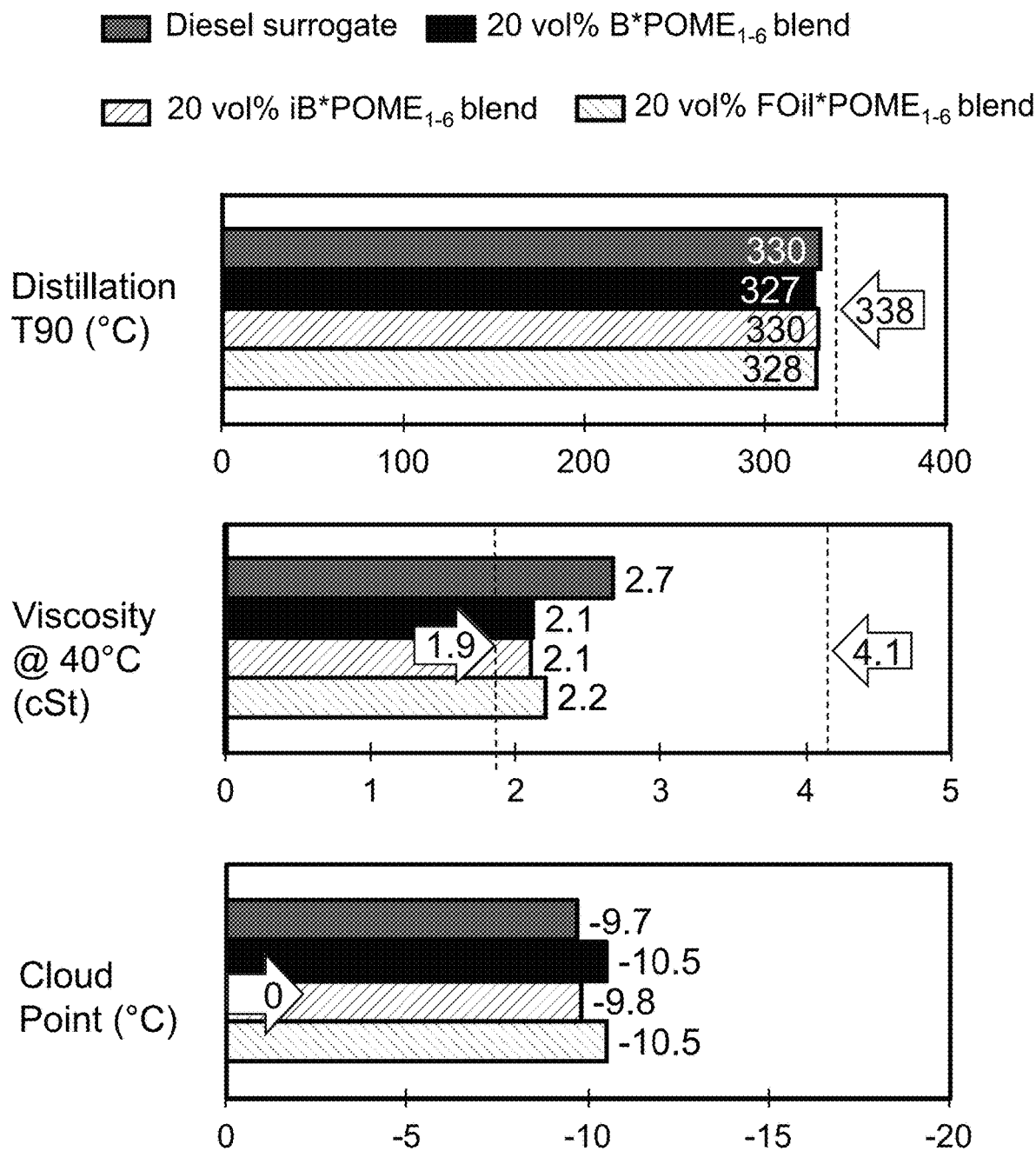
FIGS. 9A, 9B, and 9C illustrate a comparison of measured Tier 2 fuel properties of a neat base diesel fuel with the fuel properties for a 20 vol % B*POME$_{1-6}$ blended into the base diesel, the fuel properties for a 20 vol % iB*POME$_{1-6}$, and 20 vol % FOil*POME$_{1-5}$ blended into the base diesel according to some embodiments of the present disclosure. The targeted region for each fuel property is indicated by the arrow marked with the specific numerical criterion for diesel blend stocks.
Figure 9B:
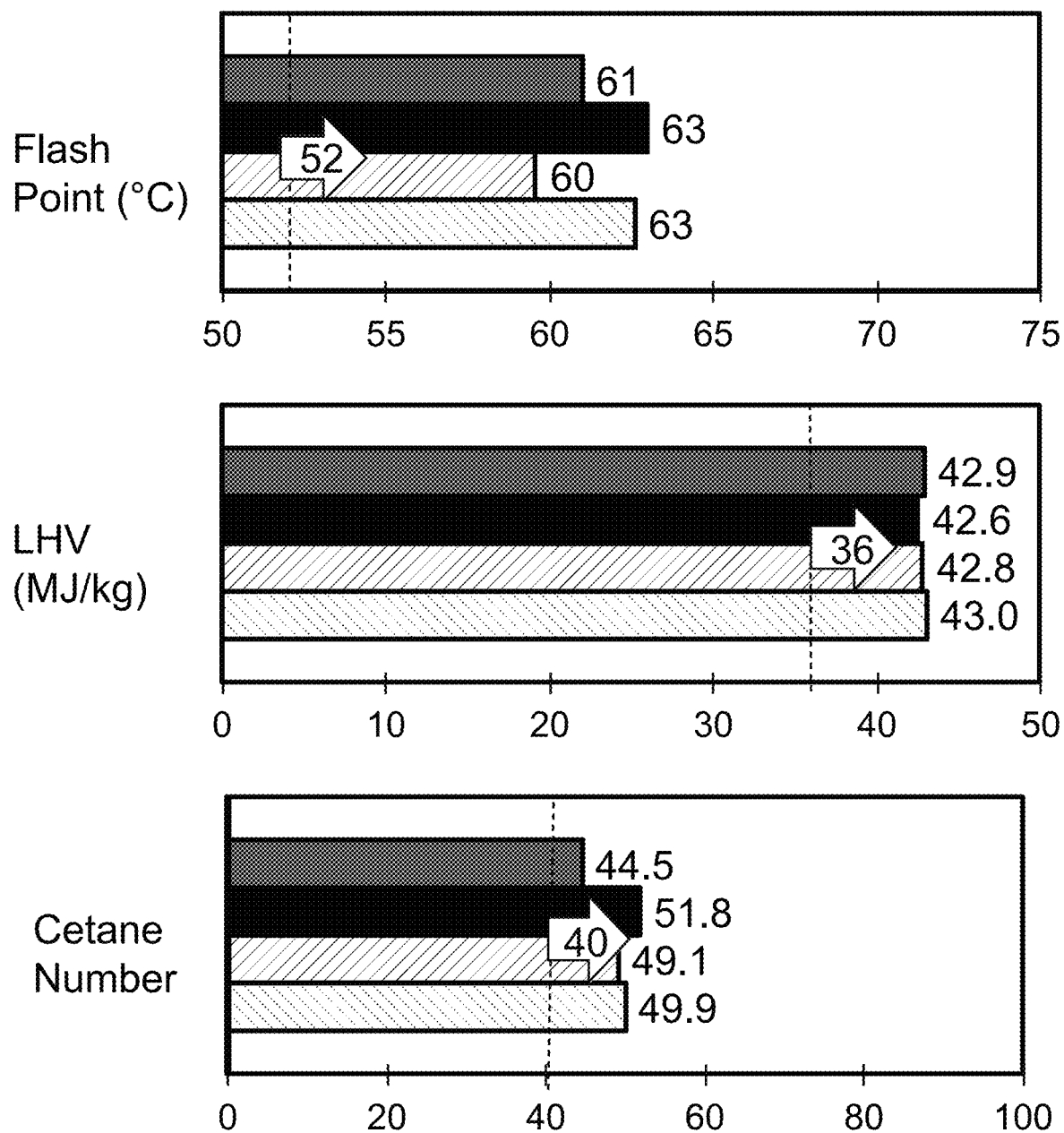
Figure 9C:
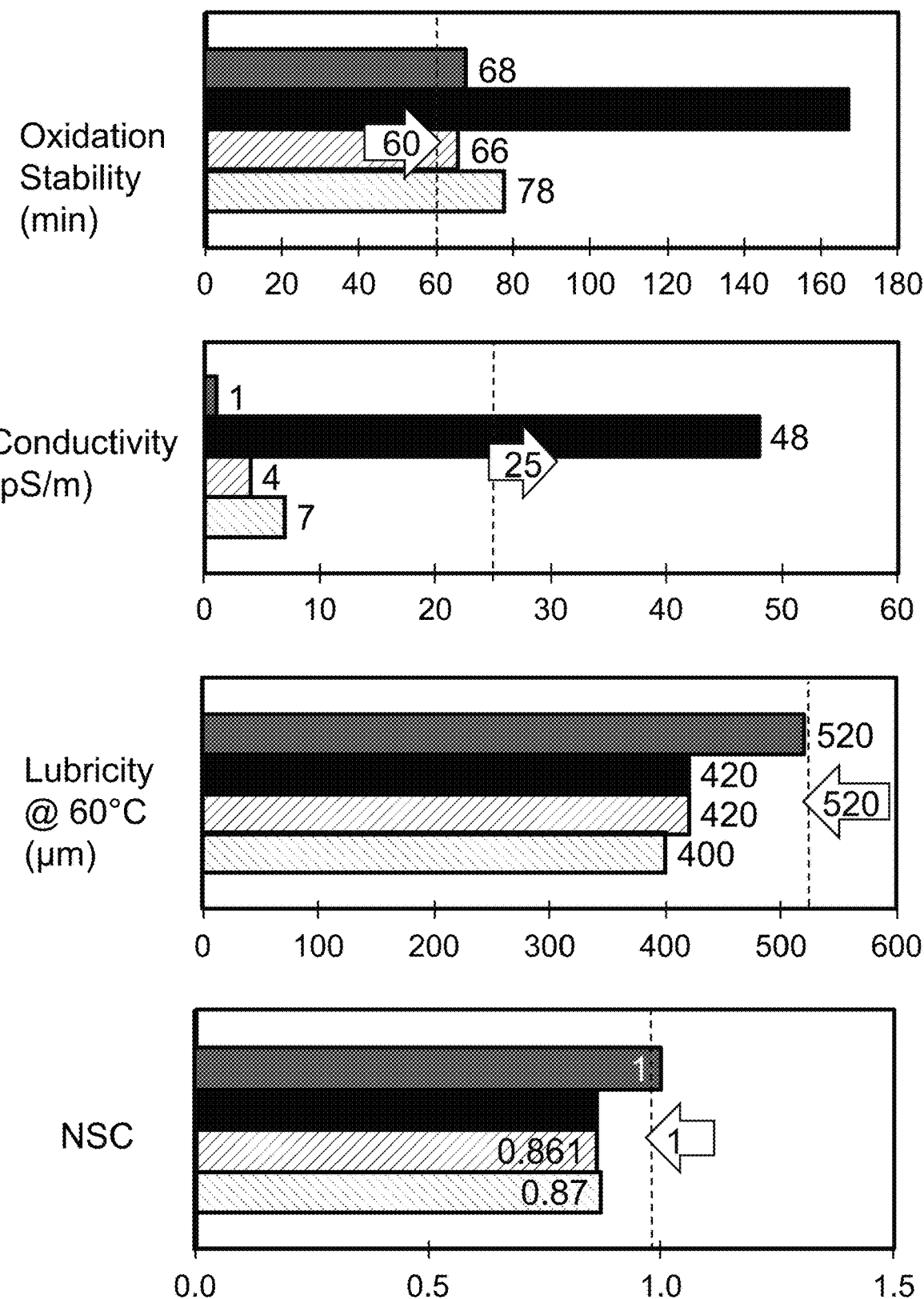

Blend property testing: The fuel properties of a 20 vol % B*POME$_{1-6}$ diesel blend were measured experimentally and compared to those of the neat base diesel. FIGS. 9A, 9B, and 9C summarize the measured fuel properties of the base diesel, and blends, and the criteria requirements. The T90 temperature of the ~20 vol % B*POME$_{1-6}$ blend (~327° C.) confirms an innocuous impact on the distillation temperature limit (~338° C.) for the Standard Specification for Diesel Fuel Oils, ASTM D975-20c. The kinematic viscosity of this blend (~2.1 cSt) was slightly lower compared to that of the base diesel (i.e., surrogate) but determined to be within the criterion range. The cloud point of the base diesel was favorably impacted with a minor decrease upon blending (about −10.5° C.); similarly, the flash point of the blend (~63° C.) showed a slight improvement compared to that of the base diesel. As expected, when blending the high-cetane B*POME$_{1-6}$, the CN was favorably increased from ~45 to ~52 at the 20 vol % blend level. The oxidation stability of the blend was evaluated by measuring its potential to oxidize and degrade, and the addition of 20 vol % of B*POME$_{1-6}$ to the base diesel resulted in a favorable improvement of the induction time from about 68 minutes to about 167 minutes.

The conductivity of the blend (~48 pS/m) was greatly improved compared to that of the base diesel, to a value almost double the minimum requirement of ~25 pS/m; this important safety metric ensures that the blend will not develop a static charge and a subsequent spark upon discharge. The lubricity of the blend, measured by the wear protection the fuel provides to fuel pumps and injectors was positively impacted by reducing the wear scar size produced during the test from 520 μm to 420 μm and further improvements are likely with common additives. The measured LHV of the blend (~42.6 MJ/kg) is comparable to that of the base diesel (~42.9 MJ/kg), meeting the criterion requirement (greater than ~36 MJ/kg) of an LHV within 10% range of commercial diesel (from ~40 MJ/kg to about 46 MJ/kg).

This demonstrates a negligible impact from the lower LHV of the neat B*POME$_{1-6}$ blend stock (~30 MJ/Kg) in the blend. The 20 vol % of B*POME$_{1-6}$ blend favorably reduced the NSC of the base diesel from 1 to 0.863 (~13.8% reduction). These results demonstrate that a 20% blend of the B*POME$_{1-6}$ blend stock has an overall favorable impact on the fuel properties of a commercial diesel improving its performance and safety ratings.

Figure 10A:
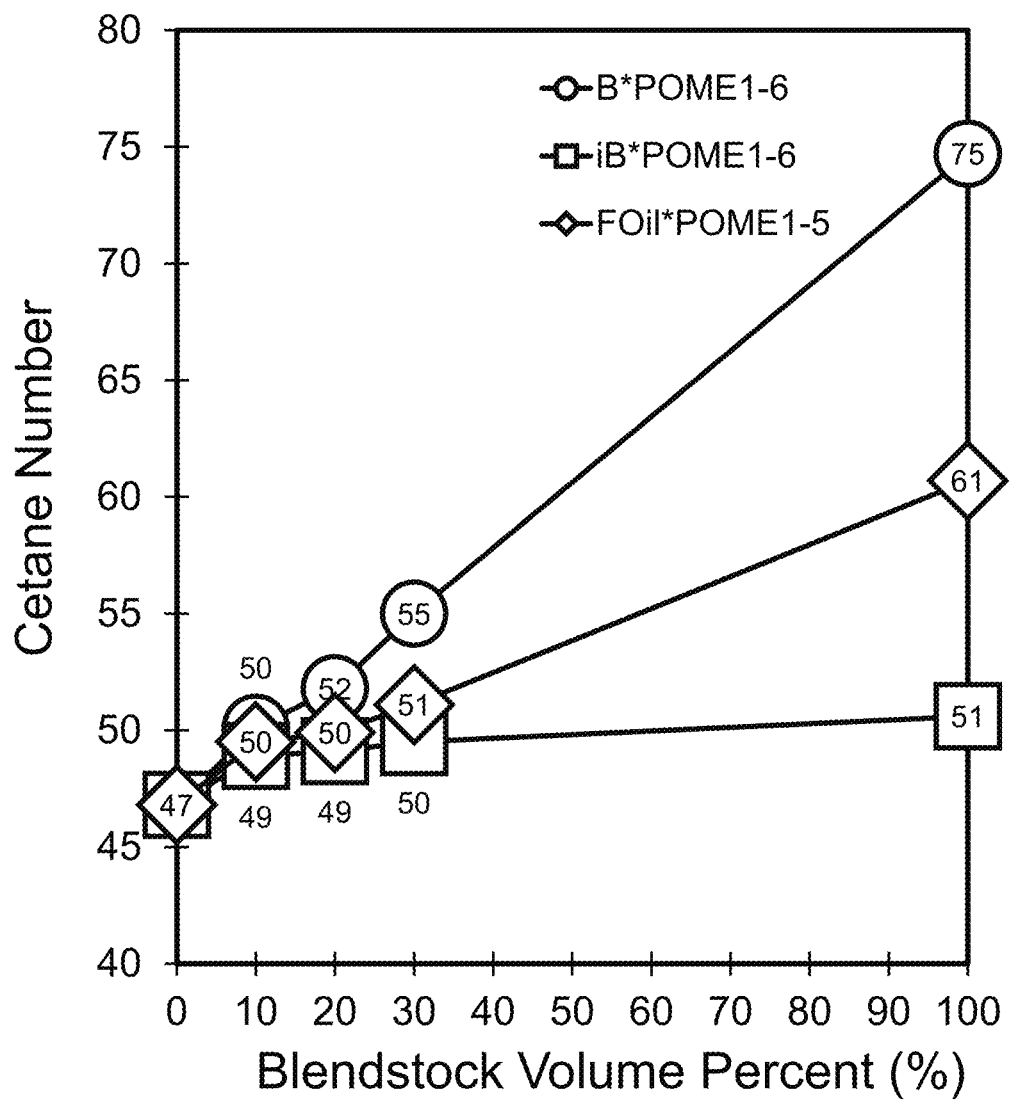
FIG. 10A illustrates Cetane Number (CN) and FIG. 10B Bolumetric Blending Cetane Number (bCNv) for 10%, 20%, and 30% POME blends into clay-treated base diesel, and the values for the neat POME components, according to some embodiments of the present disclosure.
Figure 10B:
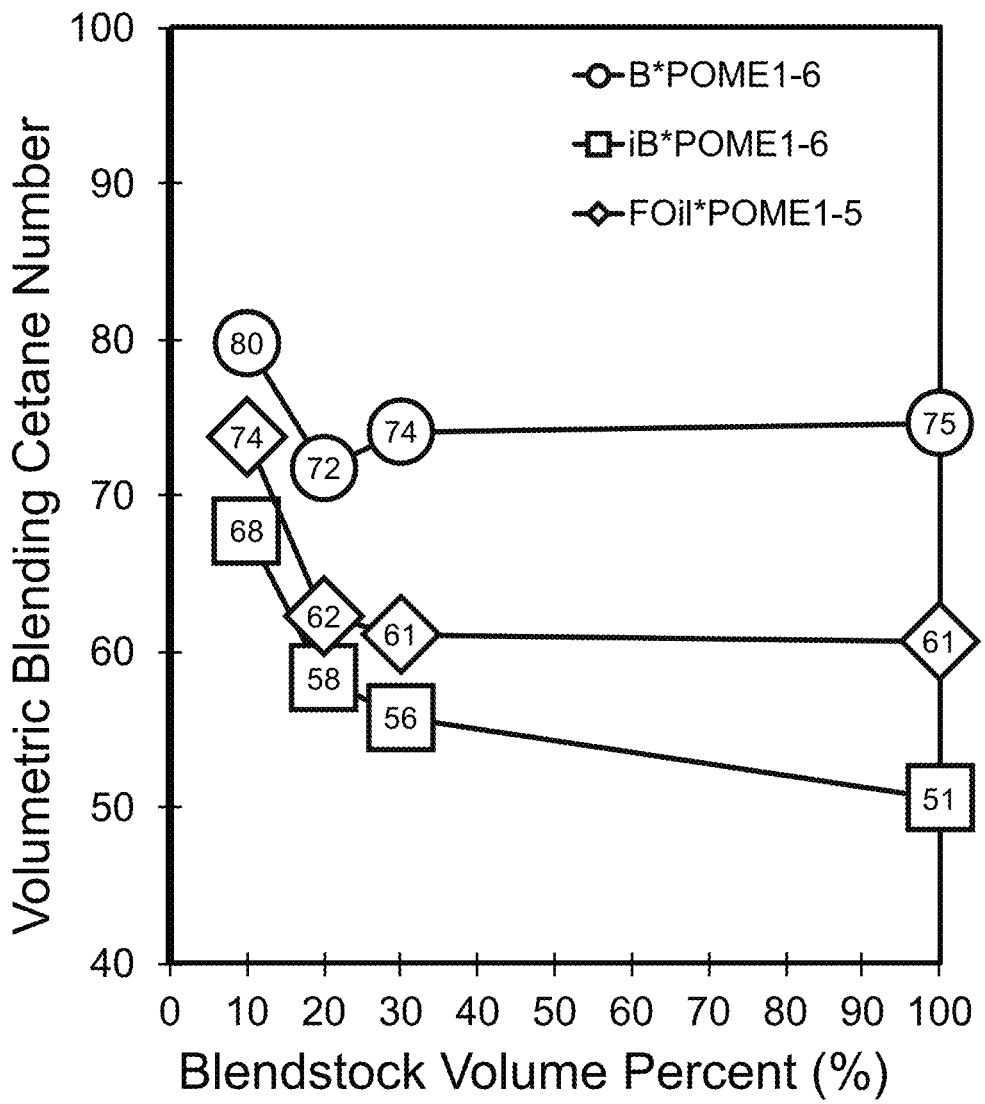

Autoignition properties at different blend levels: The observed increase in CN at the 20 vol % B*POME$_{1-6}$ blend level is advantageous, but it is also of interest to explore the effect of blend level on this critical fuel property. An analysis at blend levels between about 10 vol % and about 30 vol % B*POME$_{1-6}$ provides the Volumetric Blending Cetane Number (bCNv), and these values were compared to the CN and bCNv of the pure component (100%). The CN and bCNv data for the between about 10 vol % and about 30 vol % blends of B*POME$_{1-6}$, BB-POME$_1$ (i.e., dibutoxymethane or butylal), and the parent MM-POME$_{3-6}$ with the base diesel are presented in FIG. 10A and FIG. 10B, respectively, along with their pure component values. These additional POMEs are good reference points to the B*POME$_{1-6}$ product since BB-POME$_1$ corresponds to 46 wt. % of B*POME$_{1-6}$, and MM-POME$_{3-6}$ is the commercially available parent POME mixture having methyl end-groups from which B*POME$_{1-6}$ is derived.

Methods:

General.

Dry Amberlyst-46 (Dow Chemical Company) was used as received. 1-butanol (i.e., n-butanol) (anhydrous 99.8+%, Aldrich), and MM-POME$_{3-6}$ having the composition 45.6 wt % MM-POME$_3$, 30.4 wt % MM-POME$_4$, 17.8 wt % MM-POME$_5$, and 6.1 wt % MM-POME$_6$ (Analytik-Service GmbH) were used without any further purification. Na$_2$CO$_3$ (BioXtra≥99.0%, Sigma Aldrich) and NaHCO$_3$(Certified ACS 100.1%, Fisher Chemical) were used as received for the preparation of a 0.1 M carbonate-bicarbonate buffered aqueous solution, with a pH=9.2.

Equilibrium Calculations.

Calculation of predicted reaction equilibrium constant and product distributions were performed using Aspen Plus v10 process simulation software using the IDEAL property method. All components in the reaction system were specified as conventional components and where thermodynamic and physical property data were not available in existing Aspen Plus databanks, component properties were estimated using the National Institute of Standards and Technology ThermoDataEngine (NIST TDE) capabilities built into Aspen Plus. NIST TDE was used to estimate properties for all POMEs and hemi-acetals, with exception of methylal (MM-POME$_1$), which had existing databank entries. A feed stream consisting of a mixture of POMEs and 1-butanol set to match the appropriate molar parent POME and alcohol ratio was sent to an REQUIL reactor block set to only account for liquid-phase reactions operating isobarically at atmospheric pressure (assumed as 82.2 kPa in Golden, CO) and isothermally at 60° C. to match experimental conditions. The reactor block determines the equilibrium constant (K$_{eq}$) for each reaction at the specified temperature using the Gibbs free energy of each reaction and estimates outlet composition by solving the ideal system in the liquid phase simultaneously for all reactions using Equation 1, $$K_{eq} = \Pi_{i=products} x_i / \Pi_{i=reactants} x_i \quad (1)$$

where x$_i$ is the mole fraction of component i and a and b represent the stoichiometric coefficients of the reactants and products, respectively. Since an ideal system in the liquid phase is assumed, pressure modifications have no effect, thus outlet composition and equilibrium constant are only functions of temperature. The simulated reaction set included the formation of water and hemiacetals, but these products were not identified in the experimental product distribution. The calculated final product distribution was adjusted to only reflect products identified from experimental conditions.

End-Group Exchange Reaction.

Trans-acetalization reactions with initial molar ratios of BuOH: MM-POME$_{3-6}$ of 2:1, 4:1, and 10:1 were performed in a 100-mL round-bottom flask equipped with a reflux condenser at atmospheric pressure (in Golden, CO~82.2 kPa). A catalyst loading of 4.6 wt % with respect to the total mass of reactants was used in each reaction. As an example for the reaction with molar ratio of 2:1, reactants (12.9 mL BuOH, 10 mL MM-POME$_{3-6}$) and 1 g of catalyst were added to the flask and magnetically stirred at 350 rpm. The reaction was heated at about 60° C. for about 4 hours. The reaction mixture was then cooled to room temperature. The catalyst was separated from the products via vacuum filtration. For all experiments, a mass balance >98% was achieved and the standard error, calculated from three replicates of the 2:1 reaction, was ±1.2% (see Table 13).

TABLE 13

Standard error calculation for statistical reproducibility analysis of three trans-acetalization reactions using identical reaction conditions with 2:1 BuOH:POME$_{3-6}$ molarratio.

| ID | 2:1 (1) mol % | 2:1 (2) mol % | 2:1 (3) mol % | Average mol % | Std. Error % |
|---|---|---|---|---|---|
| MeOH + FA | 32 | 34 | 34 | 33 | 0.7 |
| BuOH | 10 | 12 | 12 | 11 | 0.7 |
| MM-POME$_1$ | 3.5 | 5.1 | 4.7 | 4.4 | 0.5 |
| MB-POME$_1$ | 22 | 18 | 18 | 19 | 1.2 |
| BB-POME$_1$ | 15 | 12 | 11 | 13 | 1.3 |
| MM-POME$_2$ | 3.5 | 2.7 | 2.7 | 3.0 | 0.2 |
| MB-POME$_2$ | 2.4 | 6.4 | 6.7 | 5.2 | 1.4 |
| BB-POME$_2$ | 3.8 | 3.4 | 3.7 | 3.6 | 0.1 |
| MM-POME$_3$ | 1.5 | 1.1 | 1.0 | 1.2 | 0.2 |
| MB-POME$_3$ | 2.4 | 2.5 | 2.3 | 2.4 | 0.1 |
| BB-POME$_3$ | 1.2 | 1.1 | 1.3 | 1.2 | 0.1 |
| MM-POME$_4$ | 0.8 | 0.5 | 0.4 | 0.6 | 0.1 |
| MB-POME$_4$ | 1.0 | 1.0 | 1.0 | 1.0 | <0.1 |
| BB-POME$_4$ | 0.3 | 0.3 | 0.4 | 0.3 | <0.1 |
| MM-POME$_5$ | 0.5 | 0.1 | 0.2 | 0.3 | 0.1 |
| MB-POME$_5$ | 0.2 | 0.2 | 0.2 | 0.2 | <0.1 |
| BB-POME$_5$ | 0.1 | 0.1 | 0.1 | 0.1 | <0.1 |
| MM-POME$_6$ | 0.2 | 0.1 | 0.1 | 0.1 | <0.1 |
| MB-POME$_6$ | 0.1 | 0.1 | 0.1 | 0.1 | <0.1 |

Separation of Diesel Boiling-Range Products.

A trans-acetalization reaction was performed as described above with a molar ratio of BuOH:MM-POME$_{3-6}$ of 2:1 using 282 mL BuOH, 218 mL MM-POME$_{3-6}$, and 21.8 g of Amberlyst-46. The crude trans-acetalization product was triple washed in equal parts by volume of a 0.1 M aqueous carbonate-bicarbonate buffer solution (pH=9.2) to remove residual water-soluble components (e.g., MeOH, formaldehyde, BuOH). After the third wash, the organic layer was dried with MgSO$_4$ and subsequently filtered. To ensure the removal of residual light components, rotary evaporation (150 rpm) at 50° C. and 50 mbar for 1 hour was performed on the washed product. The resulting liquid product was transferred to a 250-mL round-bottom flask fitted with a custom thermowell for separation in a BR Instruments Spinning Band Distillation unit. Boiling chips (ca. 30 g) were added to the distillation flask. The mixture was heated under reduced pressure (30 Torr) to distill compounds with $T_b$<160° C., and the remaining bottom fraction was collected for analysis. Gas chromatography and thermogravimetric analysis of the bottom fraction confirmed a composition of 99.7% of the desired product having a boiling range of 169-287° C. This distilled product is termed B*POME$_{1-6}$.

Product Analysis.

Molecular components of the product mixtures were identified and quantified using an Agilent 7890 gas chromatograph (GC) equipped with an HP-5MS column (30 m×250 μm×0.25 μm) and Polyarc-FID and MS detectors. Samples (1 mL) were prepared by diluting the product mixtures with acetone. The Polyarc system has a catalytic microreactor that converts all organic compounds to methane with a conversion efficiency >99.99% prior to detection by the FID. This eliminates the need for calibration of FID response for each compound.

Predicted Fuel Properties.

The predicted fuel properties of B*POME$_{1-6}$ were calculated assuming a linear blending of the predicted and measured (when available) fuel properties of each of the pure components based on either their molar fraction (for CN and YSI), mass fraction (for LHV and water solubility) or volume fraction (for $T_{flash}$ and $T_{cloud}$) with Equations 2-7, where $x_i$ is the molar fraction, $m_i$ is the mass fraction and $v_i$ is the volume fraction of each of the B*POME$_{1-6}$ components:

$$CN_{B*POME1-6} = \Sigma x_i CN_i \quad (2)$$

$$YSI_{B*POME1-6} = \Sigma x_i YSI_i \quad (3)$$

$$LHV_{B*POME1-6} = \Sigma m_i LHV_i \quad (4)$$

$$\text{Water solub}_{B*POME1-6} = \Sigma m_i \text{Water solub}_i \quad (5)$$

$$T\text{flash}_{B*POME1-6} = \Sigma v_i T\text{flash}_i \quad (6)$$

$$T\text{cloud}_{B*POME1-6} = \Sigma v_i T\text{melt}_i \quad (7)$$

Fuel Property Measurements.

Boiling point range of the target product was determined by a thermogravimetric analysis (TGA) based simulated distillation. Distillation temperatures were not determined via the standard method for diesel fuel, ASTM D86, due to the limited volume of sample available and gas chromatography based simulated distillation was not utilized given the relatively polar nature of POMEs. Analysis was conducted using a CAHN TG-131 TGA under flowing nitrogen with a ramp rate of 50° C./min from 25 to 550° C. The sample size was ca. 250 mg. The distillation parameters were selected to generate curves that closely matched ASTM D86 distillation values. The results of this method were validated using a standard fuel oil designed for validating ASTM D86 (Accustandard). Cloud point was measured using a Phase Technology Series 70X according to ASTM D5773; the method uncertainty is typically ±2.5° C. Flash point was measured according to ASTM D7094-17a with a method reproducibility stated as ±5.5° C. Indicated cetane number (ICN) was measured using an Advanced Fuel Ignition Delay Analyzer (AFIDA) instrument according to ASTM D8183-18 and where reproducibility is calculated as ±0.006407(ICN)$^{1.47}$. Higher heating value (HHV) and lower heating value (LHV) were determined according to ASTM D240-19 with a method reproducibility of ±0.4 MJ/kg.

Sooting tendencies were measured using a previously developed yield-based approach.[35] The specific procedures and apparatus used in this study were described in McEnally et al. 2019.[36] It consisted of three steps: (1) 1000 ppm of n-heptane, toluene, and each test compound were sequentially doped into the fuel of a nitrogen-diluted methane/air coflow nonpremixed flame; (2) the maximum soot concentration was measured in each flame with line-of-sight spectral radiance (LSSR); and (3) these concentrations were rescaled into a yield sooting index (YSI) defined by Equation 8:

$$YSI_{TC} = (YSI_{TOL} - YSI_{HEP}) \times \frac{LSSR_{TC} - LSSR_{HEP}}{LSSR_{TOL} - LSSR_{HEP}} + YSI_{HEP} \quad (8)$$

The subscripts TC, TOL, and HEP refer to the test compound, toluene, and n-heptane, respectively. This rescaling method removes sources of systematic uncertainty such as errors in the gas-phase reactant flow rates. Furthermore, it allows the new results to be quantitatively compared with a database that contains measured YSIs for hundreds of organic compounds. The parameters $YSI_{TOL}$ and $YSI_{HEP}$ are constants that define the YSI scale; their values—170.9 and 36.0—were taken from the database so that the newly measured YSI would be on the same scale. Each YSI was measured three times and then averaged. The systematic uncertainty in YSI is ±2%, which is dominated by the uncertainty in the mass densities of the samples. Isooctane was used as an internal standard and measured 10 times during this study. Its measured values were consistent over time with a variation of ±3.6% (2 standard deviations). Thus, the total uncertainty in the measured YSIs is ±5.6%; the average value for isooctane (63.6) agrees to within this uncertainty with earlier measurements (61.7). The diesel fuel used for comparison was the "CFA" certification fuel described in Mueller et al. (*Energy & Fuels* 2011, 25 (10), 4723-4733).

To evaluate the relative water solubility of the B*POME$_{1-6}$ product, a sample was mixed thoroughly with deionized water at a volumetric ratio of 1:5 for water: B*POME$_{1-6}$. The aqueous layer was then analyzed by total organic carbon (TOC) to determine the amount of the fuel product that was extracted into water. The aqueous phase was further characterized with gas chromatography coupled with mass spectrometry and flame ionization detection (GC-MS-FID) and compared to the parent B*POME$_{1-6}$ mixture to evaluate which components were preferentially extracted. The concentration of each component was approximated from the FID response to estimate both the total amount of fuel product and relative solubility of individual components. The B*POME$_{1-6}$ sample was diluted 1:10 in acetone for the GC-MS-FID analysis. Aqueous phases were diluted 1:2 with methanol. An Agilent 8890 GC/FID—5977B MS system was used for analysis. A volume of 1.0 μL was injected into a split/splitless inlet set to 275° C. and a split ratio of 1:100. Compounds were separated using an Rtx-50 column (50% phenyl polydimethylsiloxane, Restek) of dimensions 30 m×0.25 mm×0.25 μm with a helium carrier gas at a flow rate of 1.0 mL/min. A post column splitter was used to divert column effluent simultaneously to FID and MS detectors for qualitative and quantitative analysis. The GC oven temperature was held at 40° C. for 2 minutes, then ramped to 140° C. at 7° C./min, followed by a ramp to 290° C. at 12° C./min and held for 10 minutes. The MS transfer line and FID temperatures were set to 350° C. The MS detector was operated in continuous scan mode from m/z 29 to 300. The FID response was calibrated using a standard of 2,5-dimethylfuran prepared gravimetrically in acetone. The resultant linear response curve had an $R^2$ of 0.999.

TABLE 14

Predicted (bold) and measured fuel properties of pure components of B*POME$_{1-6}$ used to calculate the predicted fuel properties of B*POME$_{1-6}$ assuming a linear blending of the pure components based on its molar fraction (CN and YSI), mass fraction (LHV and water solubility) and volume fraction (T$_{flash}$ and T$_{cloud}$).

| ID | Cetane Number | LHV (MJ/kg) | Flash Point (° C.) | Boiling Point (° C.) | Melting Point/Cloud point for blend (° C.) | YSI | Water sol. (g/L) |
|---|---|---|---|---|---|---|---|
| BB-POME$_1$ | 67$ | 34$ | 62$ | 187$ | −58$ | 45$ | 0.3$ |
| MM-POME$_2$ | 63* | 21.2 | −4.2 | 105 | −70 | 6 | 275 |
| MB-POME$_2$ | 98 | 28 | 42 | 167 | −27 | 24 | 10 |
| BB-POME$_2$ | 108 | 31.2 | 83 | 227 | 7.5 | 41 | 0.4 |
| MM-POME$_3$ | 70* | 20# | 54# | 156# | −43# | 13 | 357 |
| MB-POME$_3$ | 108 | 26 | 71 | 209 | 2 | 25 | 13 |
| BB-POME$_3$ | 115 | 29 | 76 | 263 | 35 | 43 | 0.4 |
| MM-POME$_4$ | 90* | 19# | 88# | 202# | −10# | 16 | 441 |
| MB-POME$_4$ | 116 | 24 | 104 | 257 | 30 | 26 | 16 |
| BB-POME$_4$ | 120 | 28 | 130 | 296 | 61 | 44 | 0.5 |
| MM-POME$_5$ | 116 | 19# | 115# | 242# | 18# | 9 | 527 |
| MB-POME$_5$ | 121 | 23 | 120 | 281 | 56 | 27 | 17 |
| BB-POME$_5$ | 125 | 26 | 150 | 324 | 86 | 39 | 1 |
| MM-POME$_6$ | 122 | 18 | 109 | 265 | 52 | 11 | 614 |
| MB-POME$_6$ | 126 | 22 | 141 | 311 | 82 | 28 | 20 |
| Predicted properties of mixed butyl-exchanged POMEs | 88 | 31 | 69 | 160-324 | −23 | 37 | 14 |

Predicted values (bold) from Bartholet, et al.
$Values from Fioroni, et al.
Values from Lautenschütz, et al.
*Values from Burger et al.

TABLE 15

Computed (bold) and measured fuel properties for MM-POMEn and RR end-group exchanged-POMEs grouped by n-value.

| Species | End-groups | LHV (MJ/kg) | Water sol. (g/L)* |
|---|---|---|---|
| POME$_1$ | MM | 23# | 133 |
|  | EE | 29# | 22 |
|  | PP | 32* | 3 |
|  | BB | 34$ | 0.3$ |
| POME$_2$ | MM | 21* | 275 |
|  | EE | 26# | 31 |
|  | PP | 29* | 3 |
|  | BB | 31* | 0.4 |
| POME$_3$ | MM | 20# | 357 |
|  | EE | 24# | 39 |
|  | PP | 27* | 4 |
|  | BB | 29* | 0.4 |
| POME$_4$ | MM | 19# | 441 |
|  | EE | 23# | 47 |
|  | PP | 26* | 5 |
|  | BB | 28* | 0.5 |

*Values from Bartholet, et al.
$Values from Fioroni, et al.
Values from Lautenschtitz, et al.

TABLE 16

Experimental product distributions from trans-acetalization reactions with 2:1, 4:1 and 10:1 BuOH:MM-POME$_{3-6}$ molar ratios. Reaction conditions were 60° C., 4 hours.

|  | 2:1 | | 4:1 | | 10:1 | |
|---|---|---|---|---|---|---|
| ID | mol % | wt % | mol % | wt % | mol % | wt % |
| MeOH + FA | 33 | 10 | 14 | 3.6 | <0.1 | 0.7 |
| BuOH | 11 | 8.0 | 23 | 14 | 61 | 44 |
| MM-POME$_1$ | 3.7 | 3.2 | 3.1 | 2.0 | 3.0 | 2.2 |
| MB-POME$_1$ | 19 | 24 | 24 | 25 | 10 | 12 |
| BB-POME$_1$ | 13 | 22 | 29 | 44 | 23 | 40 |
| MM-POME$_2$ | 3.0 | 3.0 | 0.5 | 0.5 | — | — |
| MB-POME$_2$ | 5.2 | 7.9 | 2.5 | 3.3 | 0.2 | 0.2 |
| BB-POME$_2$ | 3.7 | 7.3 | 2.3 | 4.1 | 0.3 | 0.5 |
| MM-POME$_3$ | 1.2 | 1.6 | 0.9 | 1.1 | 0.2 | 0.3 |
| MB-POME$_3$ | 2.4 | 4.4 | 0.2 | 0.3 | <0.1 | <0.1 |
| BB-POME$_3$ | 1.2 | 2.8 | 0.2 | 0.3 | — | — |
| MM-POME$_4$ | 0.6 | 0.9 | 0.8 | 1.2 | 0.2 | 0.4 |
| MB-POME$_4$ | 1.0 | 2.0 | <0.1 | 0.1 | <0.1 | <0.1 |
| BB-POME$_4$ | 0.3 | 0.9 | <0.1 | <0.1 | — | — |
| MM-POME$_5$ | 0.3 | 0.7 | <0.1 | <0.1 | <0.1 | <0.1 |
| MB-POME$_5$ | 0.2 | 0.6 | <0.1 | <0.1 | <0.1 | <0.1 |
| BB-POME$_5$ | 0.1 | 0.3 | — | — | — | — |
| MM-POME$_6$ | 0.1 | 0.3 | 0.2 | 0.4 | 0.1 | 0.1 |
| MB-POME$_6$ | 0.1 | 0.2 | — | — | — | — |
| BB-POME$_6$ | <0.1 | 0.1 | — | — | — | — |

TABLE 17

Experimental crude product distributions in mol % and wt % of
trans-acetalization reactions with molar ratios of 1-butanol:MM-POME$_{3-6}$
of 2:1, 4:1 and 10:1. Methanol (MeOH) and formaldehyde (FA)
overlap in this analysis and are grouped into one entry.

| | 2:1 | | 4:1 | | 10:1 | |
|---|---|---|---|---|---|---|
| ID | mol % | wt % | mol % | wt % | mol % | wt % |
| MeOH + FA | 33% | 10% | 14% | 4% | 0.02% | 1% |
| BuOH | 11% | 8% | 23% | 14% | 61% | 44% |
| MM-POME$_1$ | 4% | 3% | 3% | 2% | 3% | 2% |
| MB-POME$_1$ | 19% | 24% | 24% | 25% | 10% | 12% |
| BB-POME$_1$ | 13% | 22% | 29% | 44% | 23% | 40% |
| MM-POME$_2$ | 3% | 3% | 1% | 0% | | |
| MB-POME$_2$ | 5% | 8% | 2% | 3% | 0.2% | 0.2% |
| BB-POME$_2$ | 4% | 7% | 2% | 4% | 0.3% | 1% |
| MM-POME$_3$ | 1% | 2% | 1% | 1% | 0.2% | 0.3% |
| MB-POME$_3$ | 2% | 4% | 0.2% | 0.3% | 0.01% | 0.02% |
| BB-POME$_3$ | 1% | 3% | 0.2% | 0.3% | | |
| MM-POME$_4$ | 1% | 1% | 1% | 1% | 0.2% | 0.4% |
| MB-POME$_4$ | 1% | 2% | 0.0% | 0.1% | 0.01% | 0.01% |
| BB-POME$_4$ | 0.3% | 1% | 0.01% | 0.02% | | |
| MM-POME$_5$ | 0.3% | 1% | 0.01% | 0.02% | 0.005% | 0.01% |
| MB-POME$_5$ | 0.2% | 1% | 0.01% | 0.02% | 0.004% | 0.01% |
| BB-POME$_5$ | 0.1% | 0.3% | | | | |
| MM-POME$_6$ | 0.1% | 0.3% | 0.2% | 0.4% | 0.1% | 0.1% |
| MB-POME$_6$ | 0.1% | 0.2% | | | | |
| BB-POME$_6$ | 0.03% | 0.1% | | | | |

TABLE 18

Calculated diesel fuel range ($T_b > 160°$ C.) product
distributions in mol % and wt % of trans-acetalization reactions
with molar ratios of 1-butanol:MM-POME$_{3-6}$ of 2:1, 4:1 and 10:1.
This product mixture includes all MM-, MB-, and BB-POMEs,
representing no aqueous extraction of MM-POMEs prior to distillation.

| | 2:1 | | 4:1 | | 10:1 | |
|---|---|---|---|---|---|---|
| ID | mol % | wt % | mol % | wt % | mol % | wt % |
| BB-POME$_1$ | 46% | 44% | 82% | 82% | 97% | 97% |
| MB-POME$_2$ | 18% | 16% | 7% | 6% | 1% | 1% |
| BB-POME$_2$ | 13% | 15% | 7% | 8% | 1% | 1% |
| MB-POME$_3$ | 9% | 9% | 1% | 1% | 0.1% | 0.1% |
| BB-POME$_3$ | 4% | 6% | 0.5% | 1% | — | — |
| MM-POME$_4$ | 2% | 2% | 2% | 2% | 1% | 1% |
| MB-POME$_4$ | 3% | 4% | 0.1% | 0.1% | 0.02% | 0.03% |
| BB-POME$_4$ | 1% | 2% | 0.03% | 0.04% | — | — |
| MM-POME$_5$ | 1% | 1% | 0.04% | 0.04% | 0.02% | 0.02% |
| MB-POME$_5$ | 1% | 1% | 0.03% | 0.04% | 0.02% | 0.02% |
| BB-POME$_5$ | 0.3% | 1% | — | — | — | — |
| MM-POME$_6$ | 0.5% | 1% | 1% | 1% | 0.2% | 0.3% |
| MB-POME$_6$ | 0.2% | 0.3% | — | — | — | — |
| BB-POME$_6$ | 0.1% | 0.2% | — | — | — | — |

TABLE 19

Calculated diesel fuel range ($T_b > 160°$ C.) product
distributions mol % and wt % of trans-acetalization reactions
with molar ratios of 1-butanol:MM-POME$_{3-6}$ of 2:1, 4:1 and 10:1.
This product mixture excludes MM-POMEs,
representing aqueous extraction prior to distillation.

| | 2:1 | | 4:1 | | 10:1 | |
|---|---|---|---|---|---|---|
| ID | mol % | wt % | mol % | wt % | mol % | wt % |
| BB-POME$_1$ | 48% | 46% | 85% | 84% | 98% | 98% |
| MB-POME$_2$ | 19% | 16% | 7% | 6% | 1% | 1% |
| BB-POME$_2$ | 13% | 15% | 7% | 8% | 1% | 1% |
| MB-POME$_3$ | 9% | 9% | 1% | 1% | 0.1% | 0.1% |
| BB-POME$_3$ | 5% | 6% | 0.5% | 1% | — | — |
| MB-POME$_4$ | 4% | 4% | 0.1% | 0.1% | 0.02% | 0.03% |

TABLE 19-continued

Calculated diesel fuel range ($T_b > 160°$ C.) product
distributions mol % and wt % of trans-acetalization reactions
with molar ratios of 1-butanol:MM-POME$_{3-6}$ of 2:1, 4:1 and 10:1.
This product mixture excludes MM-POMEs,
representing aqueous extraction prior to distillation.

| | 2:1 | | 4:1 | | 10:1 | |
|---|---|---|---|---|---|---|
| ID | mol % | wt % | mol % | wt % | mol % | wt % |
| BB-POME$_4$ | 1% | 2% | 0.03% | 0.04% | — | — |
| MB-POME$_5$ | 1% | 1% | 0.03% | 0.04% | 0.02% | 0.02% |
| BB-POME$_5$ | 0.4% | 1% | — | — | — | — |
| MB-POME$_6$ | 0.2% | 0.3% | — | — | — | — |
| BB-POME$_6$ | 0.1% | 0.2% | — | — | — | — |

TABLE 20

Predicted and experimental Tier 1 diesel fuel properties for the distilled
B*POME$_{1-6}$ product from the reaction of 1-butanol:MM-POME$_{3-6}$ having a 2:1 molar
ratio. Predicted Tier 1 diesel fuel properties for butyl-exchanged POMEs from the
reactions of 1-butanol:MM-POME$_{3-6}$ having a 4:1 or 10:1 molar ratio, based on
the product distributions in Tables 2 and 3. Predicted values were calculated using
a linear blending model of the pure component values based on mole fraction (CN and YSI),
mass fraction (LHV and water solubility), or volume fraction ($T_{flash}$ and $T_{cloud}$).

| | 2:1 (B*POME$_{1-6}$) | | 4:1 (Predicted) | | 10:1 (Predicted) | |
|---|---|---|---|---|---|---|
| Fuel Property | Predicted | Experimental | MM, MB, and BB | MB and BB | MM, MB, and BB | MB and BB |
| Cetane Number | 88 | 75 | 73 | 73 | 68 | 68 |
| LHV (MJ/kg) | 31 | 30 | 33 | 33 | 34 | 34 |
| Flash Point (° C.) | 69 | 62 | 64 | 63 | 63 | 62 |
| Cloud Point (° C.) | −23 | −27 | −48 | −50 | −56 | −57 |
| YSI | 37 | 37 | 42 | 43 | 44 | 45 |
| Water solub. (g/L) | 14.2 | 7.3 | 15.6 | 1.1 | 6.3 | 0.4 |

Fuel BLEND Property Measurements.

Alcohol-exchanged POMEs were blended at 20 vol % with a commercially obtained diesel for fuel property testing. This fuel was determined to be biodiesel free and was clay-treated to remove common additives that enhance lubricity and conductivity in the interest of objectively studying the impact of the blend stock on these properties. CN was measured for 10, 20, and 30 vol % blends into the same clay-treated diesel fuel.

Higher heating value (HHV) and lower heating value (LHV) were determined according to ASTM D240-19 with a method reproducibility of ±0.4 MJ/kg. Distillation temperatures were determined via the standard method for diesel fuel, ASTM D86-20b. Flash point was measured according to D6450-16a (2021) using an Eralytics ERA-FLASH. Viscosity at 40° C. was measured according to ASTM D445-21. Cloud point was measured using a Phase Technology Series 70X according to ASTM D5773-21. Conductivity was measured using an EMCEE Model 1152 per ASTM D2624-21. Lubricity was measured using ASTM D6079-18. Oxidation stability was measured using a PetroOxy per ASTM D7545-14(2019)el. The normalized soot concentration (NSC) was calculated with Equation 9. It is a measure of the volume-based sooting tendency of the blended B*POME$_{1-6}$, normalized to the base diesel. As shown in Equation 9, NSC=0 means a fuel produces no soot, and NSC=1 means the tested fuel produces as much soot as the base diesel. NSC avoids the uncertainty associated with the molecular weight of the base diesel fuel, and being volume-based, offers more relevant information to many applications than the mole-based YSI.

$$NSC = \frac{LSSR_{test\ fuel} - LSSR_{undoped}}{LSSR_{diesel} - LSSR_{undoped}} \quad (9)$$

Where: $LSSR_{test\ fuel}$=Maximum centerline line-of-sight spectral radiance signal of the test fuel; $LSSR_{diesel}$=Maximum centerline line-of-sight spectral radiance signal of the base diesel; and $LSSR_{undoped}$=Maximum centerline line-of-sight spectral radiance signal of the base $CH_4$—$N_2$ flame without any fuel dopant.

Indicated cetane number (ICN) was measured using an Advanced Fuel Ignition Delay Analyzer (AFIDA) instrument according to ASTM D8183-18, where reproducibility is calculated as ±0.006407(ICN)$^{1.47}$. The bCNv was calculated with Equation 10.

$$bCNv = \frac{[\text{Blend } CN - Vs * CNs]}{Vb} \quad (10)$$

Where: Blend CN=CN of the blend stock blended into the base diesel; CNs=CN of the base diesel; Vs=volume fraction of the base diesel; and Vb=volume fraction of the blend stock Composition Example Set #1

Example 1. A composition comprising: a compound having the structure $R_1O$—$(CH_2O)_n$—$R_2$; and a cetane number between about 65 and about 100, wherein: n is between 1 and 10, inclusively, $R_1$ comprises a first alkyl group, and $R_2$ comprises a second alkyl group.

Example 2. The composition of Example 1, further comprising a lower heating value between about 30 MJ/kg and about 45 MJ/kg.

Example 3. The composition of either Example 1 or Example 2, further comprising a flash point temperature between about 55° C. and about −25° C.

Example 4. The composition of any one of Examples 1-3, further comprising a cloud point temperature between about −65° C. and about 70° C.

Example 5. The composition of any one of Examples 1-4, further comprising a yield sooting index (YSI) between about 20 and about 50.

Example 6. The composition of any one of Examples 1-5, further comprising a water solubility between about 0.1 g/L and 20 g/L.

Example 7. The composition of any one of Examples 1-6, wherein $R_1$ comprises between 1 and 10 carbon atoms.

Example 8. The composition of any one of Examples 1-7, wherein $R_2$ comprises between 1 and 10 carbon atoms.

Example 9. The composition of any one of Examples 1-8, wherein $R_1$ comprises a first butyl group.

Example 10. The composition of any one of Examples 1-9, wherein the first butyl group comprises at least one of 1-butyl, iso-butyl, or sec-butyl.

Example 11. The composition of any one of Examples 1-10, wherein $R_1$ comprises a first pentyl group.

Example 12. The composition of any one of Examples 1-11, wherein the first pentyl group comprises at least one of n-pentyl, iso-pentyl, or neo-pentyl.

Example 13. The composition of any one of Examples 1-12, wherein $R_2$ comprises a second butyl group.

Example 14. The composition of any one of Examples 1-13, wherein the second butyl group comprises at least one of 1-butyl, iso-butyl, or sec-butyl.

Example 15. The composition of any one of Examples 1-14, wherein $R_2$ comprises a second pentyl group.

Example 16. The composition of any one of Examples 1-15, wherein the second pentyl group comprises at least one of n-pentyl, iso-pentyl, or neo-pentyl.

Example 17. The composition of any one of Examples 1-16, wherein n is between 1 and 6, inclusively.

Example 18. The composition of any one of Examples 1-17, wherein the first butyl group is present at a concentration between 0 mol % and 100 mol %, inclusively.

Example 19. The composition of any one of Examples 1-18, wherein the remainder of $R_1$ comprises a first methyl group.

Example 20. The composition of any one of Examples 1-19, wherein the second butyl group is present at a concentration between 0 mol % and 100 mol %, inclusively.

Example 21. The composition of any one of Examples 1-20, wherein the remainder of $R_2$ comprises a second methyl group.

Composition Example Set #2

Example 1. A composition comprising: at least one of $BuO(CH_2O)Bu$, $MeO(CH_2O)_2Bu$, or $BuO(CH_2O)_2Bu$, wherein Bu represents at least one of an n-butyl group, an iso-butyl group, or a sec-butyl group and Me represents a methyl group, and a cetane number between about 45 and about 100.

Example 2. The composition of Example 1, wherein Bu is an n-butyl group.

Example 3. The composition of either Example 1 or Example 2, wherein Bu is an iso-butyl group.

Example 4. The composition of any one of Examples 1-3, further comprising a lower heating value between about 25 MJ/kg and about 40 MJ/kg.

Example 5. The composition of any one of Examples 1-4, further comprising a water solubility less than about 10 g/L.

Example 6. The composition of any one of Examples 1-5, wherein the $BuO(CH_2O)Bu$ is present at a first concentration between about 25 wt % and about 55 wt %.

Example 7. The composition of any one of Examples 1-6, wherein the $MeO(CH_2O)_2Bu$ is present at a second concentration between about 10 wt % and about 25 wt %.

Example 8. The composition of any one of Examples 1-7, wherein the $BuO(CH_2O)_2Bu$ is present at a third concentration between about 10 wt % and about 25 wt %.

Example 9. The composition of any one of Examples 1-8, comprising $BuO(CH_2O)Bu$ and $MeO(CH_2O)_2Bu$.

Example 10. The composition of any one of Examples 1-9, further comprising $BuO(CH_2O)_2Bu$.

Example 11. The composition of any one of Examples 1-10, wherein the cetane number is determined by ASTM D975-20a.

Example 12. The composition of any one of Examples 1-11, wherein the lower heating value is determined by ASTM D240-19.

Composition Example Set #3

Example 1. A composition comprising: $PeO(CH_2O)Pe$, $MeO(CH_2O)_2Pe$, $PeO(CH_2O)_2Pe$, or $MeO(CH_2O)_3Pe$, wherein Pe represents at least one of an n-pentyl group, an iso-pentyl group, or a neo-pentyl group and Me represents a methyl group, and a cetane number between about 50 and about 100.

Example 2. The composition of Example 1, wherein Pe is an iso-pentyl group ($^iPe$).

Example 3. The composition of either Example 1 or Example 2, further comprising a lower heating value between about 25 MJ and about 40 MJ/kg.

Example 4. The composition of any one of Examples 1-3, further comprising a water solubility less than 5 g/L.

Example 5. The composition of any one of Examples 1-4, wherein $^iPeO(CH_2O)^iPe$ is present at a first concentration between about 15 wt % and about 30 wt %.

Example 6. The composition of any one of Examples 1-5, wherein the $MeO(CH_2O)_2{}^iPe$ is present at a second concentration between about 20 wt % and about 35 wt %.

Example 7. The composition of any one of Examples 1-6, wherein the $^iPeO(CH_2O)_2{}^iPe$ is present at a third concentration between about 5 wt % and about 15 wt %.

Example 8. The composition of any one of Examples 1-7, wherein the MeO(CH$_2$O)$_3$$^i$Pe is present at a fourth concentration between about 5 wt % and about 15 wt %.

Example 9. The composition of any one of Examples 1-8, comprising $^i$PeO(CH$_2$O)$^i$Pe and MeO(CH$_2$O)$_2$$^i$Pe.

Example 10. The composition of any one of Examples 1-9, further comprising $^i$PeO(CH$_2$O)$_2$$^i$Pe.

Example 11. The composition of any one of Examples 1-10, further comprising MeO(CH$_2$O)$_3$$^i$Pe.

Example 12. The composition of any one of Examples 1-11, wherein the cetane number is determined by ASTM D975-20a.

Example 13. The composition of any one of Examples 1-12, wherein the lower heating value is determined by ASTM D240-19.

Method Example Set

Example 1. A method comprising: completing a reaction comprising an ether and an alcohol to form a compound having the structure R$_1$O—(CH$_2$O)$_n$—R$_2$, wherein: n is between 1 and 10, inclusively, R$_1$ comprises a first alkyl group, and R$_2$ comprises a second alkyl group.

Example 2. The method of Example 1, wherein the reaction comprises a first step defined by

[chemical reaction scheme]

Example 3. The method of either Example 1 or Example 2, wherein the reaction further comprises a second step defined by

[chemical reaction scheme]

Example 4. The method of any one of Examples 1-3, wherein the first step and the second step occur substantially simultaneously.

Example 5. The method of any one of Examples 1-4, wherein the reaction is completed at a ratio of the alcohol to the ether between about 1:1 and about 50:1.

Example 6. The method of any one of Examples 1-5, wherein the ratio is between about 2:1 and about 10:1.

Example 7. The method of any one of Examples 1-6, wherein the alcohol comprises at least one of methanol, ethanol, propanol, iso-butanol, n-butanol, sec-butanol, iso-pentanol, n-pentanol, or neo-pentanol.

Example 8. The method of any one of Examples 1-7, wherein the reaction is completed at a temperature between about 20° C. and about 100° C.

Example 9. The method of any one of Examples 1-8, wherein the reaction is completed at a pressure between about 2 atm and 3 atm absolute.

Example 10. The method of any one of Examples 1-9, wherein the reaction is catalyzed sing a solid acid catalyst.

Example 11. The method of any one of Examples 1-10, wherein the solid acid catalyst comprises an acid functionalized polymer or resin.

Example 12. The method of any one of Examples 1-11, wherein the solid acid catalyst comprises a sulfonic acid functionalized styrenic-divinyl benzene resin.

Example 13. The method of any one of Examples 1-12, wherein the reaction is performed for a period of time between greater than zero minutes and about 24 hours.

Example 14. The method of any one of Examples 1-13, wherein the period of time is between about 5 minutes and about 6 hours.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A fuel composition comprising:
   CH$_3$O(CH$_2$O)$_n$Bu',
   Bu"O(CH$_2$O)$_m$Bu''', and
   CH$_3$O(CH$_2$O)$_z$CH$_3$, and
   a boiling point between 160° C. and 300° C., wherein:
   n is between 1 and 6, inclusively,
   m is between 1 and 6, inclusively, and
   z is between 1 and 6, inclusively, and
   each of Bu', Bu", and Bu''' is independently selected from the group consisting of an n-butyl group, an iso-butyl group, and a sec-butyl group.

2. The fuel composition of claim 1, further comprising a lower heating value (LHV) between about 30 MJ/kg and about 34 MJ/kg.

3. The fuel composition of claim 2, further comprising a flash point temperature between about 62° C. and about 69° C.

4. The fuel composition of claim 3, further comprising a cloud point temperature between about −58° C. and about 10° C.

5. The fuel composition of claim 4, further comprising a yield sooting index (YSI) between about 37 and about 45.

6. The fuel composition of claim 1, further comprising a water solubility between about 0.3 g/L and about 14 g/L.

7. A method comprising:
   reacting a first mixture with an alcohol, R—OH, to form a first fuel mixture, wherein:

the reacting comprises an acid catalyzed trans-acetalization reaction, the first mixture comprises $CH_3O(CH_2O)_zCH_3$, the fuel mixture comprises $CH_3O(CH_2O)_mR$ and $RO(CH_2O)_nR$, the fuel mixture has a boiling point between 160° C. and 300° C., m is between 1 and 6, inclusively, n is between 1 and 6, inclusively, z is between 1 and 6 inclusively, and R comprises a first alkyl group.

8. The fuel composition of claim 1, further comprising at least one of $CH_3O(CH_2O)_nPe'$ or $Pe''O(CH_2O)_mPe'''$, wherein:

each of Pe', Pe'', and Pe''' is independently selected from the group consisting of an n-pentyl group, an iso-pentyl group, and a neo-pentyl group.

9. The method of claim 7, wherein R comprises at least one of an ethyl group, an n-propyl group, an n-butyl group, an n-pentyl group, an n-hexyl group, an iso-butyl group, a sec-butyl group, an iso-propyl group, a 1-methylpropyl group, a 2-methylpropyl group, a 1-methylbutyl group, a 2-methylbutyl group, a 3-methylbutyl group, a iso-pentyl group, or a neo-pentyl group.

10. The method of claim 7, wherein, when the reacting is started, the alcohol and $CH_3O(CH_2O)_zCH_3$ are provided at a ratio between about 1:1 and about 50:1 (alcohol:$CH_3O(CH_2O)_zCH_3$).

11. The method of claim 7, wherein the reaction is catalyzed using an ion exchange resin.

12. The method of claim 7, wherein the reacting is performed at a temperature between about 20° C. and about 100° C.

13. The method of claim 7, wherein the reacting is performed at a pressure between about 1 atm and 2 atm (gauge).

14. The method of claim 7, further comprising:

after the reacting, treating the first fuel mixture, wherein:

the treating separates the first fuel mixture into a second fuel mixture and a third fuel mixture, the second fuel mixture comprises molecules having a boiling point in a range between about 160° C. and about 338° C., and the third fuel mixture comprises molecules having a boiling point outside the range.

* * * * *